United States Patent [19]
Klein et al.

[11] Patent Number: 5,599,306
[45] Date of Patent: Feb. 4, 1997

[54] METHOD AND APPARATUS FOR PROVIDING EXTERNAL PERFUSION LUMENS ON BALLOON CATHETERS

[75] Inventors: Enrique J. Klein, Los Altos; Jordan Bajor, Palo Alto; Paul Alba, San Jose; Aaron V. Kaplan, Los Altos, all of Calif.

[73] Assignee: LocalMed, Inc., Palo Alto, Calif.

[21] Appl. No.: 536,555

[22] Filed: Sep. 29, 1995

Related U.S. Application Data

[63] Continuation of Ser. No. 461,222, Jun. 5, 1995, abandoned, which is a continuation of Ser. No. 221,613, Apr. 1, 1994, abandoned.

[51] Int. Cl.$^6$ .................................................. A61M 25/00
[52] U.S. Cl. ........................ 604/96; 604/102; 604/53
[58] Field of Search .......................... 604/96, 21, 104, 604/97, 103, 52, 53, 107, 49, 28, 266, 264

[56] References Cited

U.S. PATENT DOCUMENTS

| | | |
|---|---|---|
| 3,173,418 | 3/1965 | Baran . |
| 3,394,705 | 7/1968 | Abramson . |
| 3,938,502 | 2/1976 | Bom . |
| 4,292,974 | 10/1981 | Fogarty et al. . |
| 4,323,071 | 4/1982 | Simpson et al. . |
| 4,327,721 | 5/1982 | Goldin et al. . |
| 4,406,656 | 9/1983 | Hattler et al. . |
| 4,417,576 | 11/1983 | Baran . |
| 4,437,856 | 3/1984 | Valli . |

(List continued on next page.)

FOREIGN PATENT DOCUMENTS

| | | |
|---|---|---|
| WO92/11890 | 7/1992 | WIPO . |
| WO92/11895 | 7/1992 | WIPO . |
| WO93/21985 | 11/1993 | WIPO . |
| 9321985 | 11/1993 | WIPO . |
| WO94/11053 | 5/1994 | WIPO . |
| WO94/11048 | 5/1994 | WIPO . |
| WO95/03082 | 2/1995 | WIPO . |
| WO95/03081 | 2/1995 | WIPO . |

OTHER PUBLICATIONS

Bom, N. et al. "Early and recent intraluminal ultrasound devices," 1989, Internal Journal of Cardiac Imaging 4:79–88.

Advanced Cardiovascular Systems, Inc., Temecula, California, "ACS Rx Perfusion™ Coronary Dilatation Catheter," 1990, (Product Brochure) pp. 1–23.

Hong, M. K. et al. "A New PTCA Balloon Catheter With Intramural Channels For Local Delivery of Drugs at Low Pressure," 1992, Supplement to Circulation, Abstracts From the 65th Scientific Sessions, vol. 86, No. 4, #1514.

EndoSonics, Pleasanton, California, "The Cathscanner® Intracoronary Imaging System," 1992, (Product Brochure).

Scimed®, Maple Grove, Minnesota, "Dispatch™," 1994, (Product Brochure).

ACS Rx Perfusion™ Coronary Dilatation Catheter, from Advanced Cardiovascular Systems, Inc., Temecula, CA, package insert copyright 1990.

Product literature from Scimed Life Systems, Inc., May 1994, Dispatch™.

*Primary Examiner*—Randall L. Green
*Assistant Examiner*—Perry E. Van Over
*Attorney, Agent, or Firm*—Townsend and Townsend and Crew LLP

[57] ABSTRACT

A catheter sleeve includes a radially expansible distal region having a plurality of axial blood perfusion lumens or channels formed thereon. The catheter sleeve may be introduced over a conventional angioplasty balloon catheter with the expansible region lying over the balloon. When the balloon of the angioplasty catheter is expanded, the perfusion lumens will provide a flow path for blood around the expanded balloon. Optionally, the catheter sleeve may further include drug infusion lumens over the radially expansible region. In this way, drugs can be delivered over prolonged periods while the underlying angioplasty balloon is inflated and blood flows through the lumens or channels to perfuse the distal myocardium.

85 Claims, 16 Drawing Sheets

U.S. PATENT DOCUMENTS

| | | |
|---|---|---|
| 4,576,177 | 3/1986 | Webster, Jr. . |
| 4,661,094 | 4/1987 | Simpson . |
| 4,681,564 | 7/1987 | Landreneau . |
| 4,693,243 | 9/1987 | Buras . |
| 4,744,790 | 5/1988 | Jankowski et al. . |
| 4,762,129 | 8/1988 | Bonzel . |
| 4,775,371 | 10/1988 | Mueller, Jr. . |
| 4,790,315 | 12/1988 | Mueller, Jr. et al. . |
| 4,841,977 | 6/1989 | Griffith et al. . |
| 4,850,358 | 7/1989 | Millar . |
| 4,850,969 | 7/1989 | Jackson . |
| 4,877,031 | 10/1989 | Conway et al. . |
| 4,892,519 | 1/1990 | Songer et al. . |
| 4,911,163 | 3/1990 | Fina . |
| 4,917,097 | 4/1990 | Proudian et al. . |
| 4,950,232 | 9/1990 | Ruzicka et al. . |
| 4,976,689 | 12/1990 | Buchbinder et al. . |
| 4,994,033 | 2/1991 | Shockey et al. . |
| 5,000,734 | 3/1991 | Boussignac et al. . |
| 5,007,897 | 4/1991 | Kalb et al. . |
| 5,009,636 | 4/1991 | Wortley et al. . |
| 5,015,232 | 5/1991 | Maglinte . |
| 5,019,042 | 5/1991 | Sahota . |
| 5,021,044 | 6/1991 | Sharkawy . |
| 5,034,001 | 7/1991 | Garrison et al. . |
| 5,041,089 | 8/1991 | Mueller et al. . |
| 5,046,497 | 9/1991 | Millar . |
| 5,049,132 | 9/1991 | Shaffer et al. . |
| 5,087,244 | 2/1992 | Wolinsky et al. . |
| 5,087,247 | 2/1992 | Horn et al. . |
| 5,092,877 | 3/1992 | Pinchuk . |
| 5,102,390 | 4/1992 | Crittenden et al. . |
| 5,102,415 | 4/1992 | Guenther et al. . |
| 5,112,305 | 5/1992 | Barath et al. . |
| 5,163,921 | 11/1992 | Feiring . |
| 5,180,364 | 1/1993 | Ginsburg . |
| 5,180,366 | 1/1993 | Woods . |
| 5,180,368 | 1/1993 | Garrison . |
| 5,192,307 | 3/1993 | Wall . |
| 5,203,338 | 3/1993 | Jang . |
| 5,213,576 | 5/1993 | Abiuso et al. . |
| 5,219,326 | 6/1993 | Hattler . |
| 5,219,335 | 6/1993 | Willard et al. . |
| 5,226,888 | 7/1993 | Arney . |
| 5,242,396 | 9/1993 | Evard . |
| 5,254,089 | 10/1993 | Wang . |
| 5,257,974 | 11/1993 | Cox . |
| 5,266,073 | 11/1993 | Wall . |
| 5,281,200 | 1/1994 | Corso, Jr. et al. . |
| 5,282,785 | 2/1994 | Shapland et al. . |
| 5,284,473 | 2/1994 | Calabria . |
| 5,295,962 | 3/1994 | Crocker et al. . |
| 5,300,085 | 4/1994 | Yock . |
| 5,306,250 | 4/1994 | March et al. . |
| 5,308,356 | 5/1994 | Blackshear, Jr. et al. . |
| 5,318,535 | 6/1994 | Miraki . |
| 5,344,401 | 9/1994 | Radisch et al. . |
| 5,358,487 | 10/1994 | Miller . |
| 5,364,356 | 11/1994 | Höfling . |
| 5,370,617 | 12/1994 | Sahota . |
| 5,378,237 | 1/1995 | Boussignac et al. . |
| 5,395,333 | 3/1995 | Brill . |
| 5,415,637 | 5/1995 | Khosravi . |
| 5,425,709 | 6/1995 | Gambale . |
| 5,433,706 | 7/1995 | Abiuso . |
| 5,439,445 | 8/1995 | Kontos . |

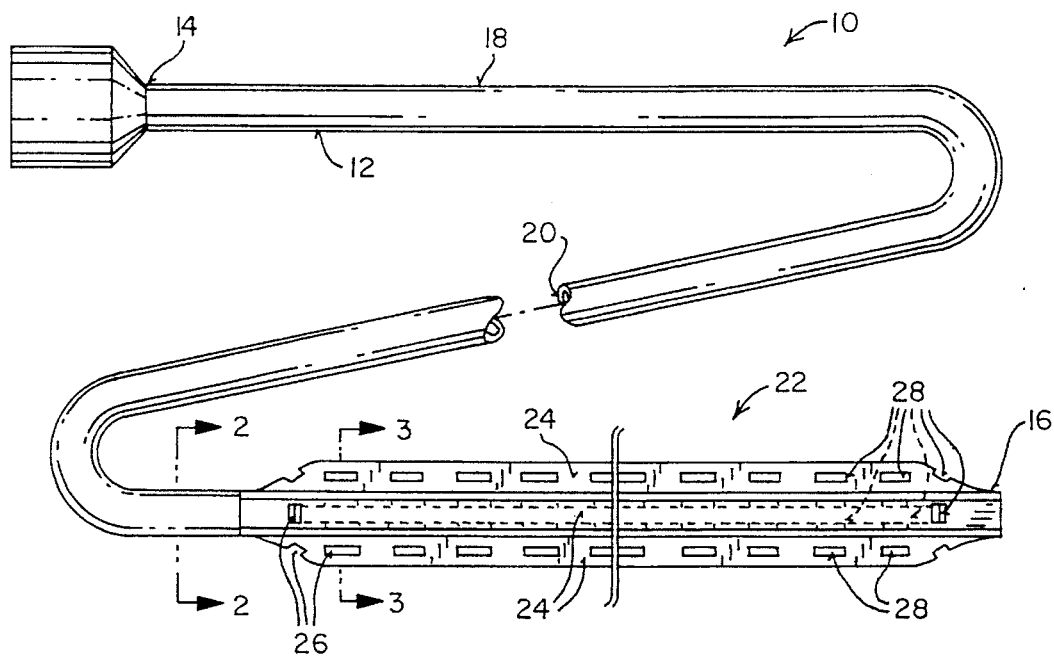
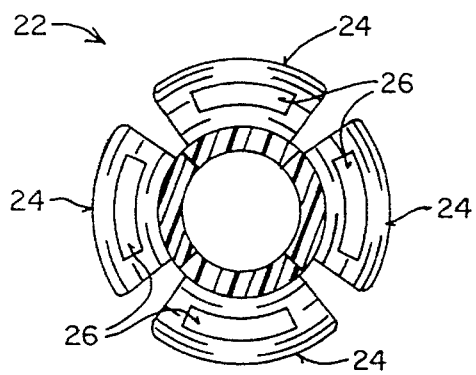 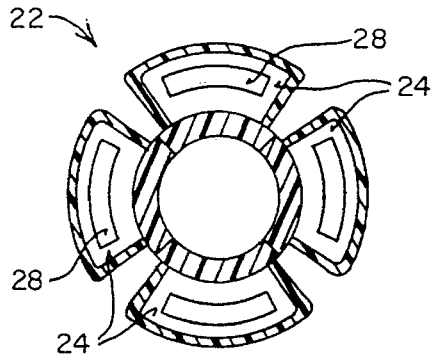
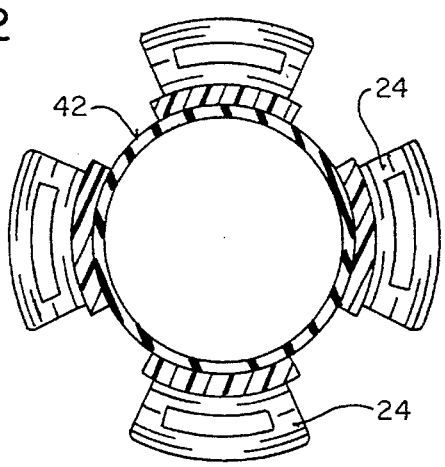

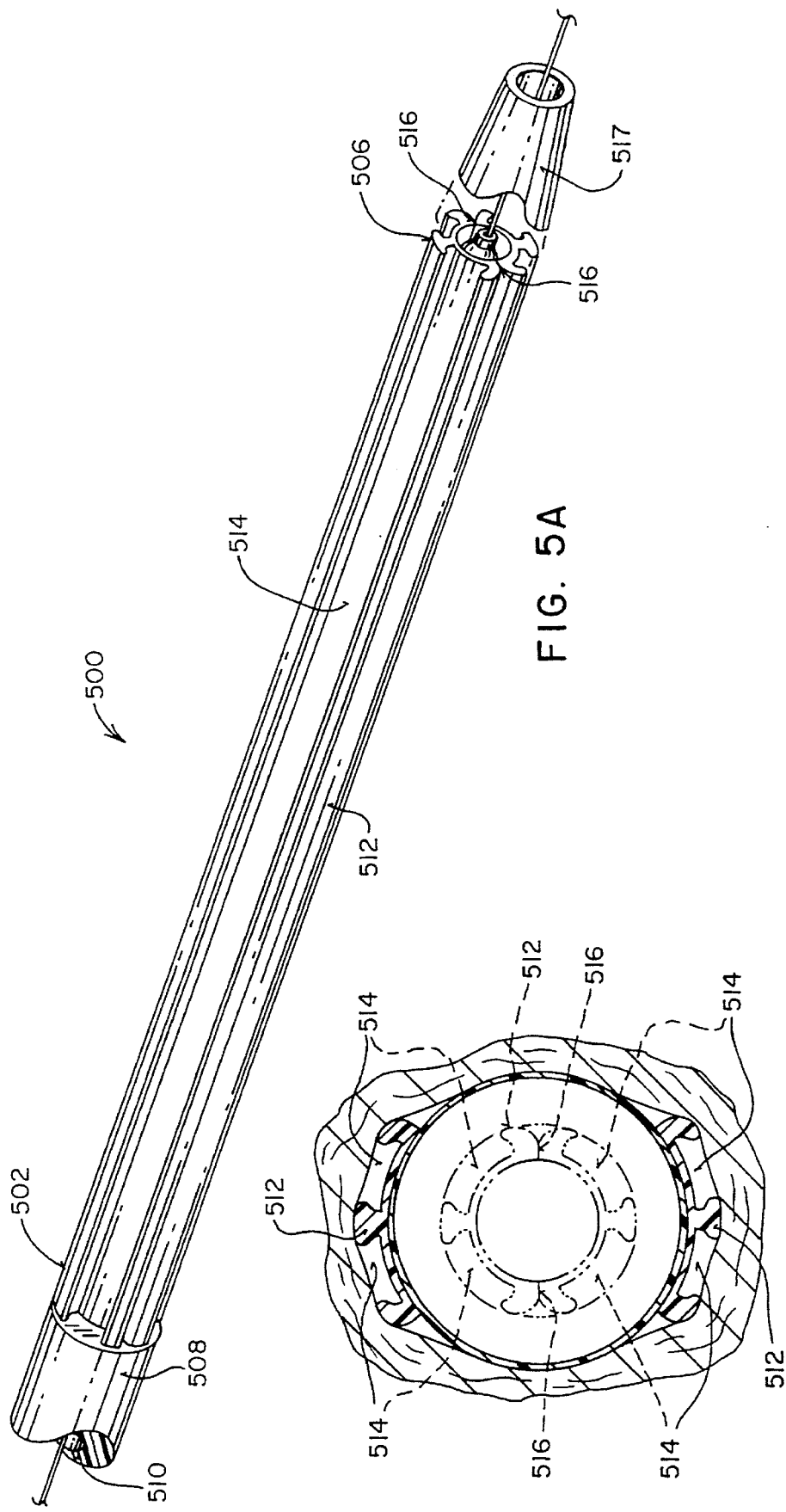

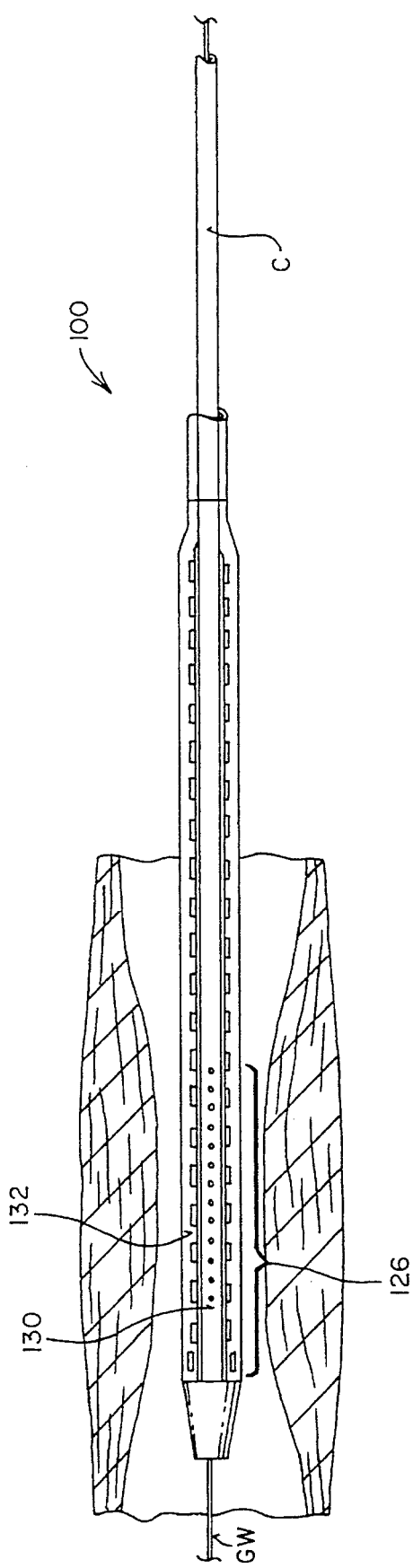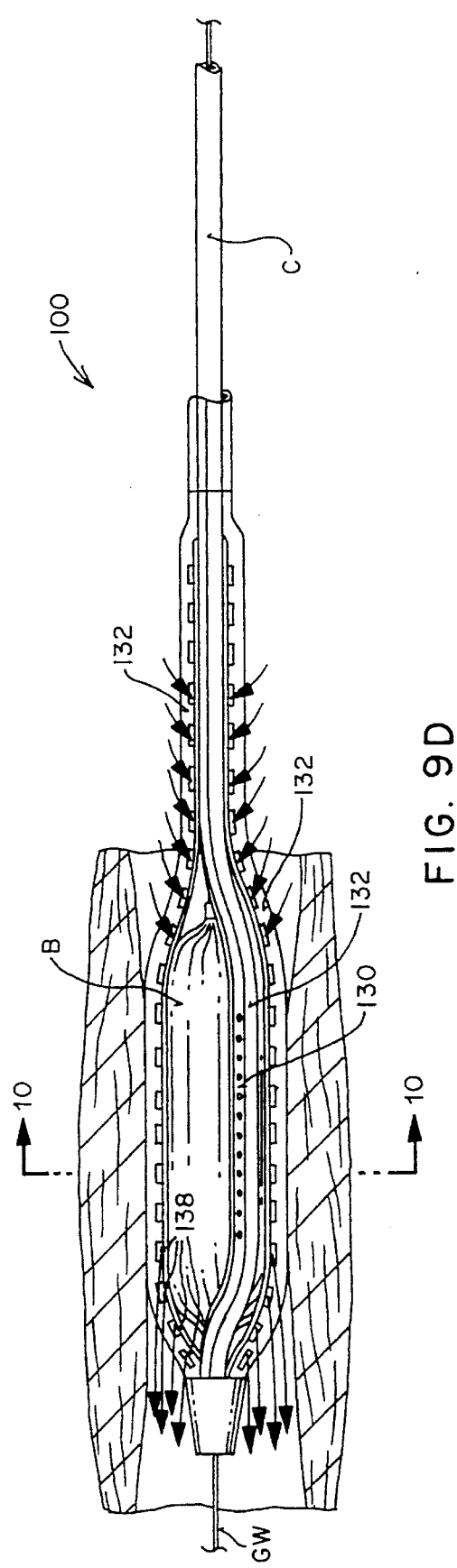

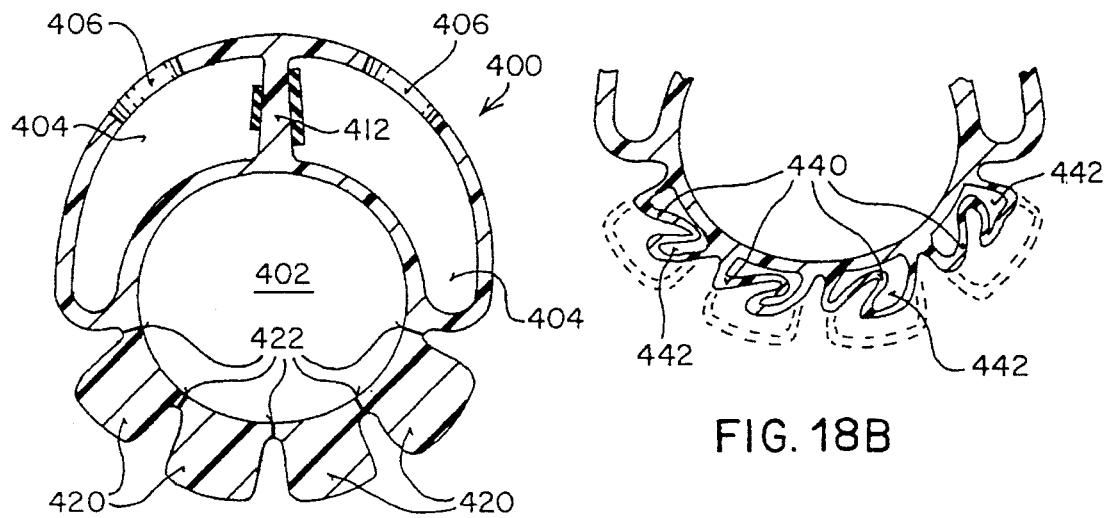
FIG. 18A
FIG. 18B
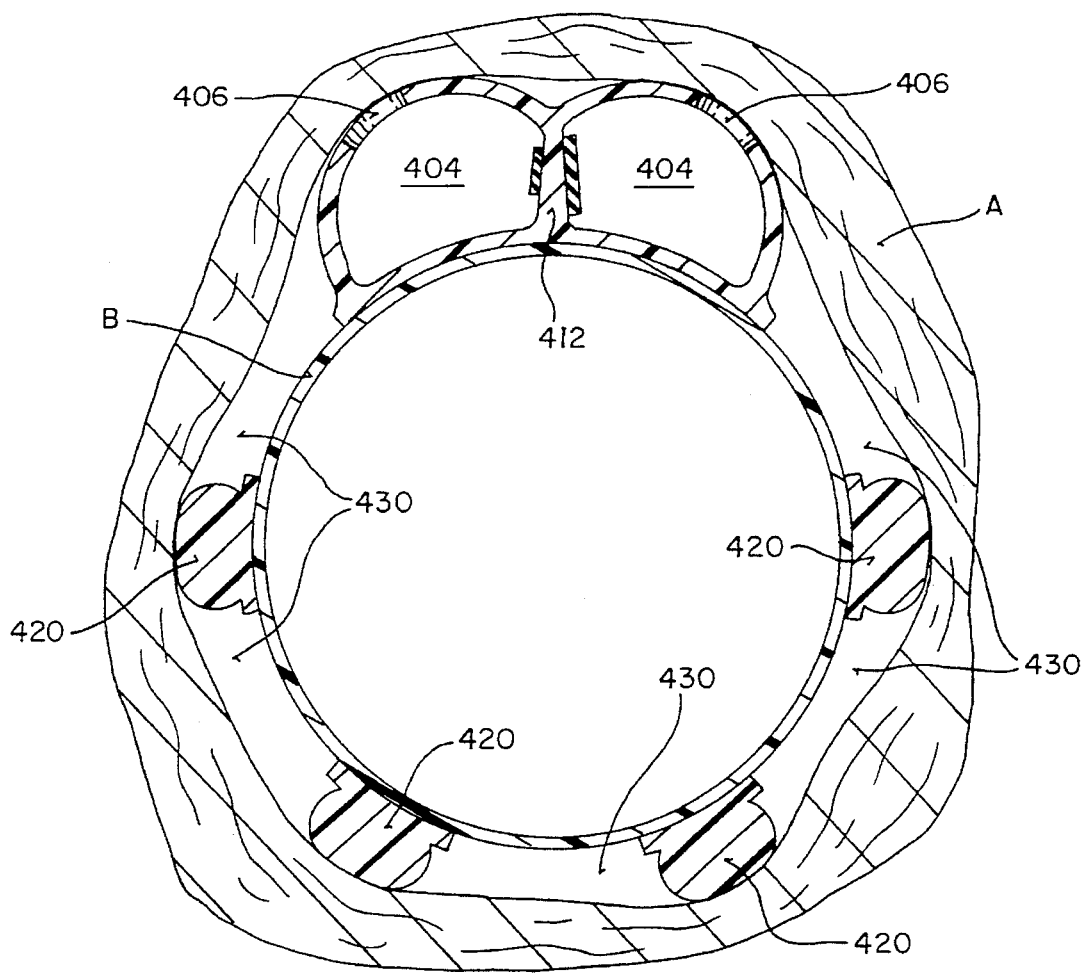
FIG. 18C

METHOD AND APPARATUS FOR PROVIDING EXTERNAL PERFUSION LUMENS ON BALLOON CATHETERS

This is a Continuation of application Ser. No. 08/461,222, filed Jun. 5, 1995, now abandoned which is a Continuation of application Ser. No. 08/221,613, filed Apr. 1, 1994, now abandoned.

CROSS-REFERENCE TO RELATED APPLICATION

This application is related to application Ser. No. 08/222,143, filed on the same day as the present application, the full disclosure of which is incorporated herein by reference.

BACKGROUND OF THE INVENTION

1. Field of the Invention

This invention relates generally to intravascular dilatation devices, and more specifically to intravascular catheters to provide blood flow during dilatation and other therapeutic procedures.

In percutaneous transluminal angioplasty procedures, a catheter having an expansible distal end, usually in the form of a balloon, is positioned in a lumen of a blood vessel with the distal end disposed within a stenotic atherosclerotic region of the vessel. The expansible end is then expanded to dilate the vessel and restore adequate blood flow through the diseased region. During dilatation blood flow is interrupted, limiting inflation time to between 0.5 and 3 minutes.

While angioplasty has gained wide acceptance, it continues to be limited by two major problems, abrupt closure and restenosis. Abrupt closure refers to the acute occlusion of a vessel immediately after or within the initial hours following the dilatation procedure. This complication, occurring in approximately one in twenty cases, frequently results in myocardial infarction and death if blood flow is not quickly restored. At present, arterial dissections, one of the causes of abrupt closure, are treated by prolonged balloon inflations lasting more than 5 minutes. Special angioplasty balloon catheters which allow for perfusion through the dilatation catheter during inflation are required for this purpose. Restenosis refers to the re-narrowing of an artery after an initially successful angioplasty. Restenosis usually occurs within the initial six months after angioplasty and afflicts approximately one in three cases. Therefore, approximately one in three patients will require additional revascularization procedures. Many different strategies have been tried unsuccessfully to reduce the restenosis rate, including mechanical (e.g., prolonged balloon inflations, atherectomy, laser and stenting) and pharmacologic (e.g., calcium antagonists, ace inhibitors, fish oils, steroids and anti-metabolic) approaches. One promising new strategy is to delivery agent directly to the arterial wall at the site of angioplasty. Several devices have been developed to deliver agent locally into the arterial wall. Similar to angioplasty balloon catheters, balloon deployed drug delivery catheters interrupt blood flow, limiting the time available to deliver agent.

Thus, it would be desirable to provide perfusion capabilities to angioplasty catheters and to agent delivery devices for the treatment of abrupt closure and restenosis and other purposes.

2. Description of the Background Art

A drug delivery catheter having an internal blood perfusion lumen and external drug delivery balloon is described in WO93/21985. Vascular drug delivery catheters are described in U.S. Pat. Nos. 5,087,244; 4,994,033; 5,021,044; and 5,112,305. U.S. Pat. Nos. 5,087,247; 4,892,519; and 4,790,315, describe angioplasty balloon catheters having integral blood perfusion capability. U.S. Pat. No. 4,661,094, describes a blood perfusion catheter intended primarily to provide blood flow through an occluded blood vessel. U.S. Pat. Nos. 5,163,921 and 5,180,364, describe guiding catheters having perfusion flow ports at their distal ends. Angioplasty catheters having integral blood perfusion capability are commercially available, e.g., under the tradename ACS Rx Perfusion™ Coronary Dilatation Catheter, from Advanced Cardiovascular Systems, Inc., Temecula, Calif., as described in a package insert copyright 1990.

SUMMARY OF THE INVENTION

According to the present invention, methods and apparatus are provided for establishing perfusion blood flow during balloon angioplasty, vascular drug delivery, and related procedures. In a preferred embodiment, the method and apparatus provide perfusion blood flow during an intravascular drug infusion procedure where a plurality of drug infusion lumens and blood perfusion lumens are radially expanded and engaged against a treatment site using a conventional balloon angioplasty catheter. In this way, prolonged drug infusion can be performed while maintaining adequate blood perfusion to tissue distal to the site of the procedure.

Apparatus according to the present invention comprise a catheter sleeve including a flexible tubular body. The flexible tubular body has a proximal end, a distal end, and a central lumen for slidably receiving a balloon angioplasty catheter therethrough. A portion of the flexible tubular body is radially expansible, usually comprising a plurality of axial slits formed near the distal end of the catheter body. In this way, an angioplasty catheter having its balloon disposed within the axially slit portion of the catheter will be able to significantly expand the catheter sleeve. By providing blood flow perfusion means, typically in the form of axial external flow paths comprising channels and/or tubular members having open lumens, over the radially expansible portion, blood perfusion flow can be established over the exterior surface of an angioplasty balloon during drug delivery procedures, prolonged balloon expansion to treat arterial dissection, and the like. In contrast with previous balloon perfusion catheter designs, where flow is established internally through an interior lumen of the catheter, the present invention establishes flow over the outside wall of the balloon, thus permitting use with even the smallest diameter (lowest profile) balloon angioplasty catheters. Additionally, such external lumens or channels permit perfusion to branch vessels which is not possible with catheters having internal perfusion lumens.

Preferably, additional axial lumens will be provided on the sleeve for infusing drugs therethrough. In this way, prolonged drug infusion therapy can be effected using a conventional balloon angioplasty catheter for radial expansion of the catheter sleeve. While axial channels or lumens will generally be preferred for both the blood perfusion function and the drug infusion function, it will be appreciated that other means external to the catheter sleeve could also be provided for establishing the necessary flow paths. For example, helical channels or lumens could be formed over, or annular lumens or compartments could be formed within, the radially expansible wall of the catheter sleeve in order to provide the desired flow paths.

Methods according to the present invention include both balloon expansion and drug delivery procedures to treat arterial dissection and for other purposes. For expansion (i.e., tacking up dissections) only, the catheter sleeve is used as described above and need only include blood perfusion lumens. A conventional balloon angioplasty catheter is used within the catheter sleeve to provide the support necessary for the treatment of arterial dissection. Balloon inflation pressures will typically be less than those associated with balloon dilatation, usually from 0.5 atm to 5 atm, but may be up to 16 atm. For drug delivery, the catheter sleeve will include both the blood perfusion flow paths and one or more lumens for drug delivery. A balloon angioplasty catheter can be used within the catheter sleeve to expand the blood perfusion flow paths and the drug delivery lumens, usually at pressures sufficient to maintain contact between the drug infusion lumens and the interior wall of the blood vessel.

In addition to its primary usefulness in providing perfusion during prolonged expansion and/or drug delivery protocols, the catheter sleeves of the present invention can be advantageously used during conventional and complex balloon angioplasty procedures. By placing the expansible portion of the sleeve directly over the dilatation balloon following the primary angioplasty procedure, prolonged inflations can be maintained with the balloon inflated at low pressure to preserve the initial inflation perimeter of the balloon. Alternatively, use of higher inflation pressures with the sleeve catheter can increase the effective size of the balloon. The use of the sleeve to provide a larger dilatation perimeter can eliminate the need to exchange balloon catheters to increase size, as often required for tacking up dissections.

In a preferred catheter sleeve intended for drug infusion and simultaneous blood perfusion, infusion lumens and blood perfusion lumens are formed in pairs on the radially expansible portion of the catheter sleeve with a common wall therebetween. Axial slits are provided between adjacent pairs of drug infusion/blood perfusion lumens, and the lumen pairs may then be radially expanded using a conventional angioplasty balloon catheter as described above. Such pairing of the drug infusion lumens and blood perfusion lumens is advantageous since it minimizes the number of walls and amount of material necessary to form the catheter sleeve, permitting fabrication of a catheter sleeve having a minimum profile or diameter.

A further understanding of the nature and advantages of the invention will become apparent by reference to the remaining portions of the specification and drawings.

BRIEF DESCRIPTION OF THE DRAWINGS

FIG. 1 is a side view of a blood perfusion catheter sleeve constructed in accordance with the principles of the present invention.

FIG. 2 is a cross-sectional view of the catheter sleeve of FIG. 1, taken along line 2—2.

FIG. 3 is a cross-sectional view of the catheter sleeve of FIG. 1, taken along line 3—3.

FIG. 4 is a cross-sectional view of the radially expansible portion of the catheter of FIG. 1, shown in its expanded configuration with a dilatation balloon therein.

FIGS. 5A and 5B illustrate an alternate embodiment of a catheter sleeve constructed in accordance with the principles of the present invention.

FIGS. 9A–9D illustrate an exemplary method of the present invention utilizing the catheter sleeve of FIG. 6 in combination with a balloon angioplasty catheter for performing an angioplasty procedure followed by drug infusion.

FIGS. 18A–18C illustrate a blood perfusion catheter similar to that illustrated in FIGS. 16–18 and having spacer bars on a side opposite to the pair of perfusion lumens.

DETAILED DESCRIPTION OF SPECIFIC EMBODIMENTS

Figure 5:
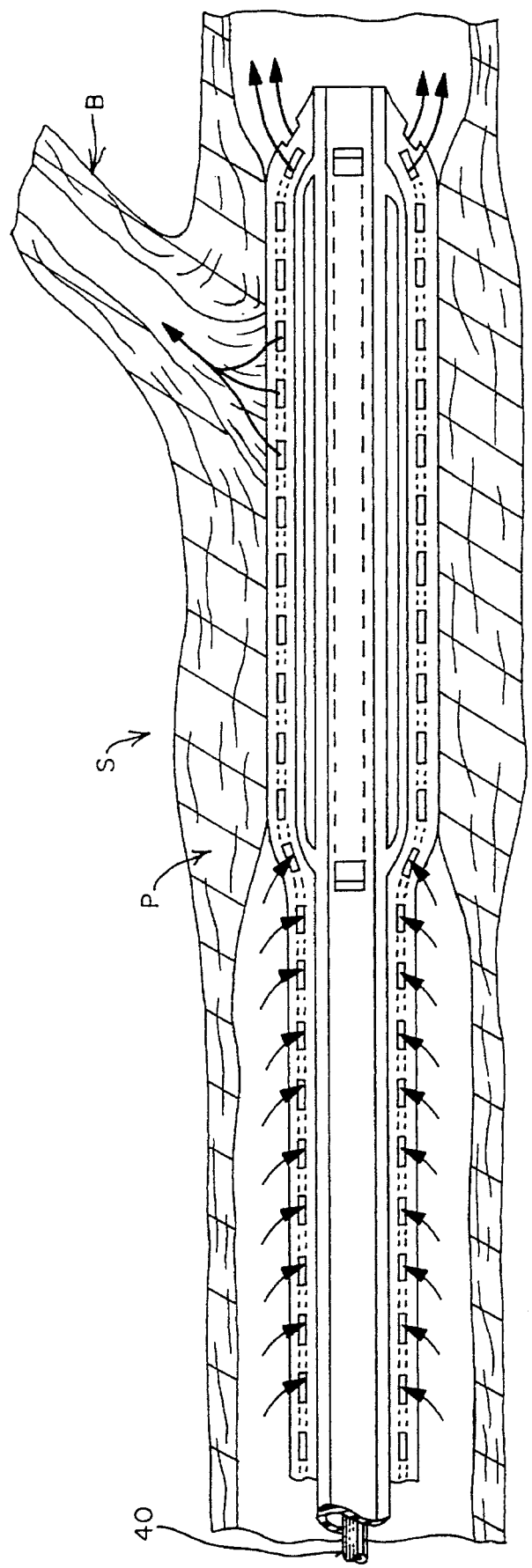
FIG. 5 illustrates the catheter sleeve of FIG. 1 in use with a balloon dilatation catheter in treating a region of stenosis within a blood vessel.

Catheter sleeves according to the present invention will comprise a flexible tubular body which may be formed from a single extrusion or from multiple extrusions which are joined either in tandem or in parallel, as described in more detail hereinbelow. The overall dimensions of the catheter body will depend on use, with the length varying widely, typically being between about 40 cm and 150 cm, usually being between about 40 cm and 120 cm for peripheral catheters and being between about 110 cm and 150 cm for coronary catheters. The diameter of the flexible tubular body will be selected to be compatible with a dilatation catheter with which it is to be used. Most importantly, the flexible tubular body of the present invention will have a central lumen having a diameter which is sufficient to accommodate passage of the uninflated balloon of the angioplasty catheter when passing therethrough.

As described in more detail hereinbelow, at least a portion of the catheter body will be radially expansible to permit expansion of the dilatation balloon therein. In addition, other portions of the flexible tubular body may be radially expansible to facilitate passage of the balloon in its uninflated configuration therethrough. The inner diameter of the flexible tubular body will typically be in the range from about 1 mm to 3 mm. More typically being in the range from about 1.3 mm to 2.0 mm.

The flexible tubular body may be composed of a wide variety of biologically compatible material, typically being formed from natural or synthetic polymers, such as polyvinylchloride, polyurethanes, polyesters, polyethylenes, polytetrafluoroethylene (PTFE's), and the like, with elastomeric portions of the body being formed from natural rubber, silicone rubber, and the like. Optionally, the catheter body may be formed as a composite having one or more reinforcement layers incorporated within its elastomeric body in order to enhance strength, flexibility, and toughness, particularly within the portion which is not radially expansible. Exemplary reinforcement layers include wire mesh, metal braid, and the like. The flexible tubular body will normally be formed by conventional extrusion of a desired polymeric material, forming the central lumen as well as one or more additional lumens, as described in more detail hereinbelow. The various lumen diameters can be modified if desired by heat expansion and shrinkage using conventional techniques. Specific techniques for forming the vascular catheters of the present invention are well described in the patent and medical literature.

At least a portion of the catheter body will be radially expansible. By "radially expansible," it is meant that the catheter body will be capable of expanding in an outward, radial direction when an expansion force is applied in the central lumen, e.g., by expansion of a dilatation balloon of a conventional angioplasty catheter. Usually, the inside diameter of the radially expansible portion of the flexible tubular body will initially be in the range from 1 mm to 3 mm and will be expansible up to 4 mm or more, consistent with commercially available balloon dilatation catheters. Such radial expansibility may be provided by forming the catheter body wholly or partly from an elastomeric material, e.g., silicone rubber. Alternatively, and preferably, such expansibility will be provided by forming a plurality of axial slits in the catheter body, resulting in segments of the catheter body which will separate upon radial expansion. Other methods for forming radially expansible tubular bodies include involuted folds, overlapping C-shaped sections, accordion folds, and the like.

Frequently, it may be desirable to form the catheter body into distinct axial segments having the same or different mechanical properties and which may be composed of different materials. For example, it may be desirable to form a proximal segment of the catheter body from a flexible, but non-radially expansible, material and structure. A radially expansible distal segment can then be joined to the distal end of the proximal segment. Alternatively, it may be desirable to provide a different number of lumens in the distal region of the catheter sleeve than in the proximal region. This can be achieved using different extrusions of the same or different materials. An example of such a structure is described in connection with FIGS. 6–10.

In a particular embodiment descirbed in connection with FIG. 18D below, a proximal portion of the catheter sleeve body is formed by a narrow diameter rod or tube which will be disposed in parallel with the dilatation catheter within the guiding catheter. The rod or tube will typically have a diameter in the range from 0.0005 mm to 0.001 mm, usually being composed of a flexible metal, such as stainless steel.

The attaching tube or rod will provide the ability to axially advance or retract the catheter sleeve over the balloon catheter, with the necessary perfusion lumens being formed on the distal sleeve portion only. By utilizing hypotube as the proximal portion of the catheter sleeve body, a lumen can be provided for drug delivery or other purposes.

One or more flow paths will be provided over the radially expansible portion of the flexible tubular body in order to establish perfusion flow therethrough when the catheter sleeve is placed in a blood vessel and the expansible portion expanded by a dilatation balloon, as described in more detail hereinafter. Conveniently, the flow paths are provided by one or more axial lumens disposed on or in the radial expansible portion of the tubular wall, preferably being formed as integral or discrete perfusion tubes over the tubular wall or as open flow channels over the tubular wall. In the case of perfusion tubes, one or more flow ports will be provided at a proximal end of said tubes in order to permit the inflow of blood to the axial lumen within the tube, and one or more ports will be provided near the distal end of the perfusion tube in order to provide for blood outflow. Preferably, ports will also be distributed along the entire length of the perfusion tubes in order to allow perfusion to arterial branch vessels, as described in connection with FIG. 5, below. In some cases, it may be necessary that the axial lumens be reinforced in order to prevent lumen compression or even collapse. Blood flowing within the perfusion lumens will be at physiologic pressure, i.e., about 80 mmHg which is approximately equal to 0.1 atm. The perfusion tubes, however, will be exposed to elevated external pressures resulting from the balloon inflation which urges the perfusion tubes against the radially stretched inner vessel wall. Sufficient reinforcement may be necessary in order to prevent compression or collapse under such elevated pressures. Suitable reinforcement structures will provide sufficient hoop strength while being sufficiently flexible in the transverse and longitudinal direction so that they permit easy placement of the catheter sleeve within a blood vessel. Suitable structures include flexible mechanical scaffolding, usually in the form of helices, spirals, and the like, as well as hydraulic scaffolding where a pressurized fluid is introduced into additional closed lumens within the catheter sleeve body.

In a preferred aspect of the present invention, additional flow paths will be provided on the radially expansible region of the flexible catheter body in order to permit drug infusion therethrough. Such drug infusion flow paths will typically be in the form of axial lumens, more typically being in the form of axial tubes formed over the catheter body. In the case of drug infusion, it is necessary that these axial lumens and/or tubes be connected to a proximal end of the tubular body so that the desired drug can be fed to the lumens. This may be accomplished with lumens formed along the entire length of the flexible tubular body, or alternatively with a single lumen over the proximal portion of the tubular body connected to two or more drug infusion tubes via a manifold.

The perfusion flow paths will typically extend over a length of the flexible tubular body which is substantially greater than that which is radially expanded. The radially expansible portion need only be about 1.5 cm to 5 cm in length to accommodate most conventional angioplasty balloons. The perfusion flow paths may be much longer, typically being at least 10 cm, usually being from 12 cm to 30 cm. Most or all of the additional length will usually (although not necessarily) be on the proximal side of the radially expansible segment so that there is ample opportunity for blood to enter the flow paths upstream of the balloon when expanded.

Referring now to FIG. 1, a first embodiment of a catheter sleeve 10 intended for providing blood perfusion flow in connection with arterial dissection treatment following balloon angioplasty is described. The catheter sleeve 10 comprises flexible tubular body 12 having a proximal end 14 and a distal end 16. The flexible tubular body includes a proximal portion 18 which is in the form of a tube having a single, central lumen 20. The flexible tubular body 12 further includes a radially expansible distal portion 22 which comprises four discrete blood perfusion lumens 24, as best observed in FIGS. 2 and 3. Each perfusion lumen 24 includes a plurality of ports 26 spaced apart axially along its length. In this way, blood perfusion can be established through the lumens 24 by entering through the proximal-most ports 26 and flowing out through the distal-most ports 28, as illustrated by arrows in FIG. 5.

Referring to FIGS. 4 and 5, expansion of the radially expansible distal portion of catheter sleeve 10 will be described. A conventional balloon angioplasty catheter 40 having balloon 42 (shown in its expanded condition in FIG. 4), is disposed within the expansible distal portion 22 of the sleeve. The balloon 42 is expanded, forcing perfusion lumens 24 radially outward and into contact with the interior of the blood vessel, typically in a region of stenosis S which has previously been dilated and which is now being treated to inhibit abrupt vessel closure resulting from arterial dissection. Thus, contact with the blood vessel wall can be maintained for an extended period of time without occlusion of the blood primary vessel P or branch vessel B. In a preferred aspect of the present invention, the treating physician can assure that perfusion is directed to the branch vessel by introducing contrast medium and repositioning the catheter/sleeve combination until one or more side ports 26 are aligned with the branch vessel and flow is observed.

As best seen in FIG. 5, only the distal most portion of the perfusion tubes 24 is radially expanded by the dilatation balloon 42. Often, the entire distal portion 22 of the flexible tubular body 12 will be axially slit between adjacent perfusion lumens 24 over the entire length of said lumens, e.g., 10 cm to 30 cm, but the portion which is actually radially expanded will be determined by the length of the dilatation balloon which is inflated therein, typically from 1.5 cm to 5 cm. The extra length of the perfusion lumens will enhance perfusion flow as described above.

FIGS. 5A and 5B illustrate an alternate embodiment of a catheter sleeve 500 constructed in accordance with the principles of the present invention. The catheter sleeve 500 comprises a flexible tubular body 502 having a proximal end (not illustrated) and a distal end 506. The flexible tubular body 502 includes a proximal portion 508 which is in the form of a tube having a central lumen 510. The body 502 further includes a radially expansible distal portion 512 (typically formed as a separate extrusion and subsequently joined to the proximal portion 508) having four perfusion channels 514 formed over its periphery. The distal portion 512 will be axially split, typically along a pair of opposed axial lines 516, allowing the resulting halves to be expanded by an internal dilatation balloon 520, as illustrated in FIG. 5B, where the cross-section of the distal portion 512 is shown in an expanded configuration in full line and a non-expanded configuration in broken line. A soft distal tip 517 is secured to the distal end of the distal portion 512, and the proximal end of the distal section is secured to the proximal portion 508. Thus, both ends of the distal section are constrained as the middle portion is expanded by a balloon, as shown in FIG. 5B.

The use of open channels 514 in place of closed lumens having a plurality of perfusion ports is advantageous since blood can enter and/or exit the channels at any point along the length where the channel is exposed to blood flow. Such increased access facilitates aligning the catheter sleeve with branch blood vessels. An additional advantage of the embodiment of FIGS. 5A and 5B is an increase in the flow area available for perfusion in comparison to designs with fully enclosed lumens. Such increase results from elimination of the outer wall of an enclosed lumen, which decreases the total amount of sleeve material which occupies the interior of the blood vessel. Such a decrease in occupied area leaves more room available for perfusion.

Figure 6:
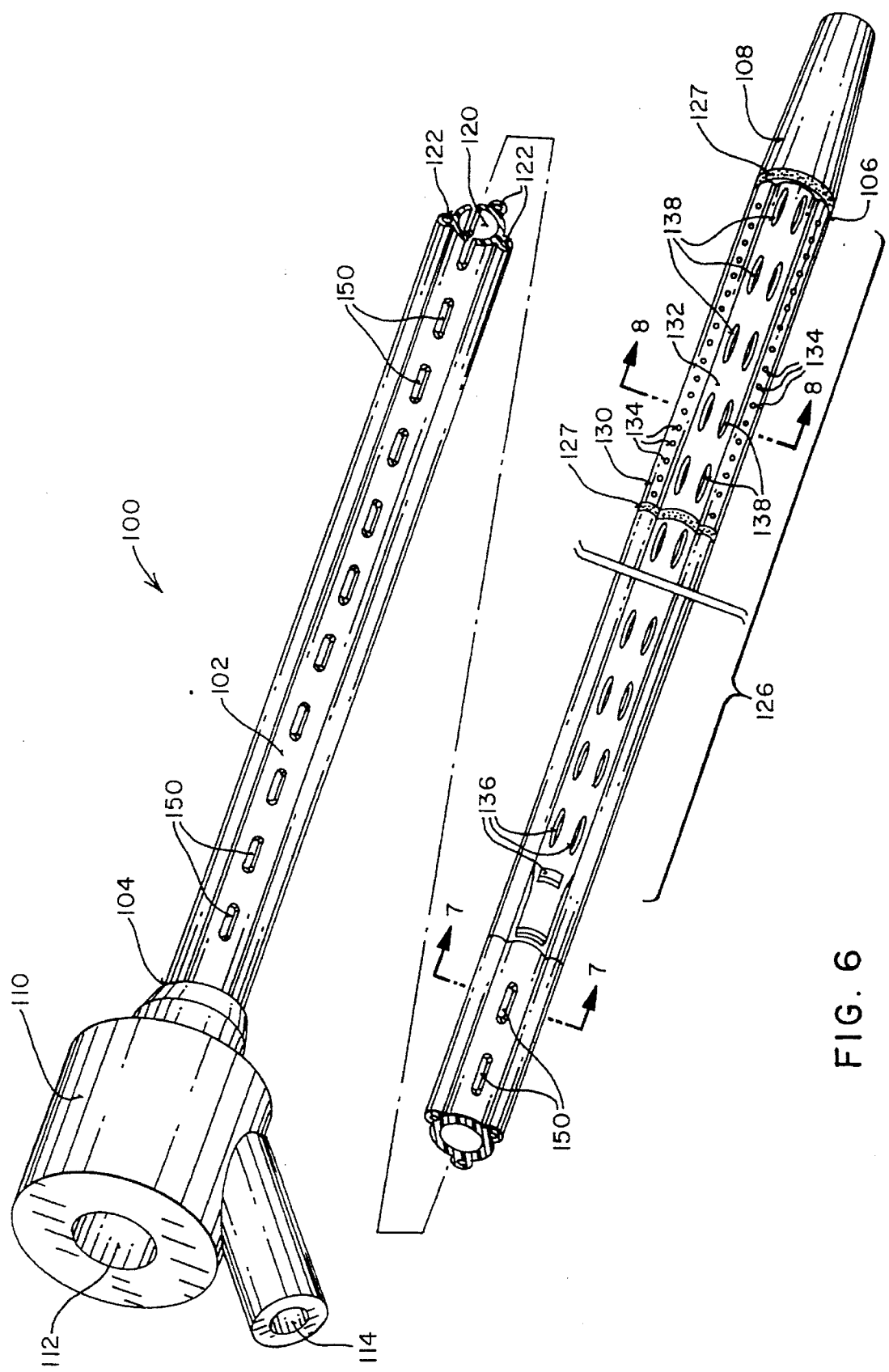
FIG. 6 is a perspective view of a preferred catheter sleeve constructed in accordance with the principles of the present invention and combining both blood perfusion and drug infusion capabilities.
Figure 7:
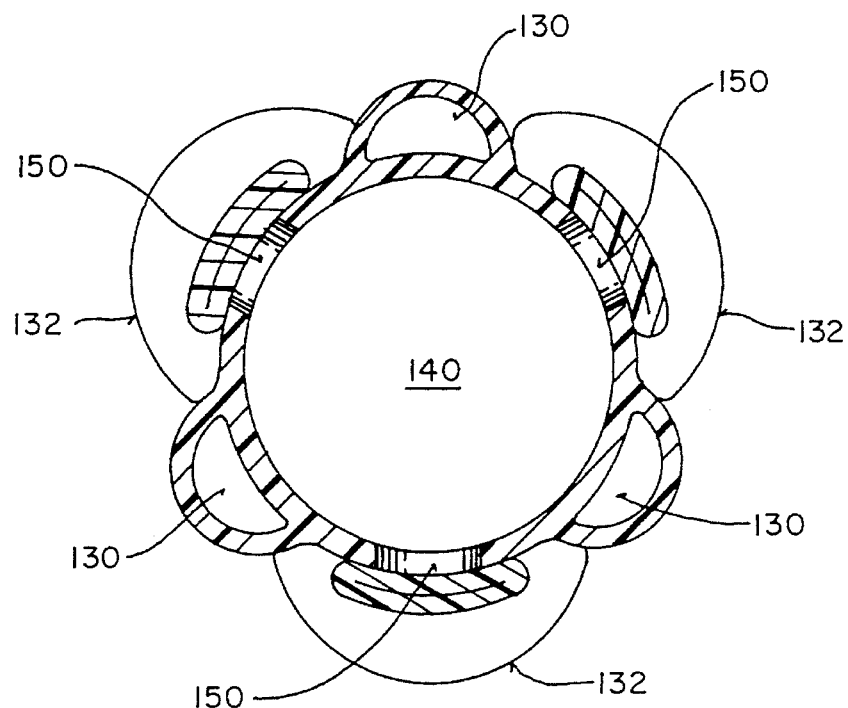
FIG. 7 is a cross-sectional view of the catheter sleeve of FIG. 6, taken along line 7—7 of FIG. 6.
Figure 8:
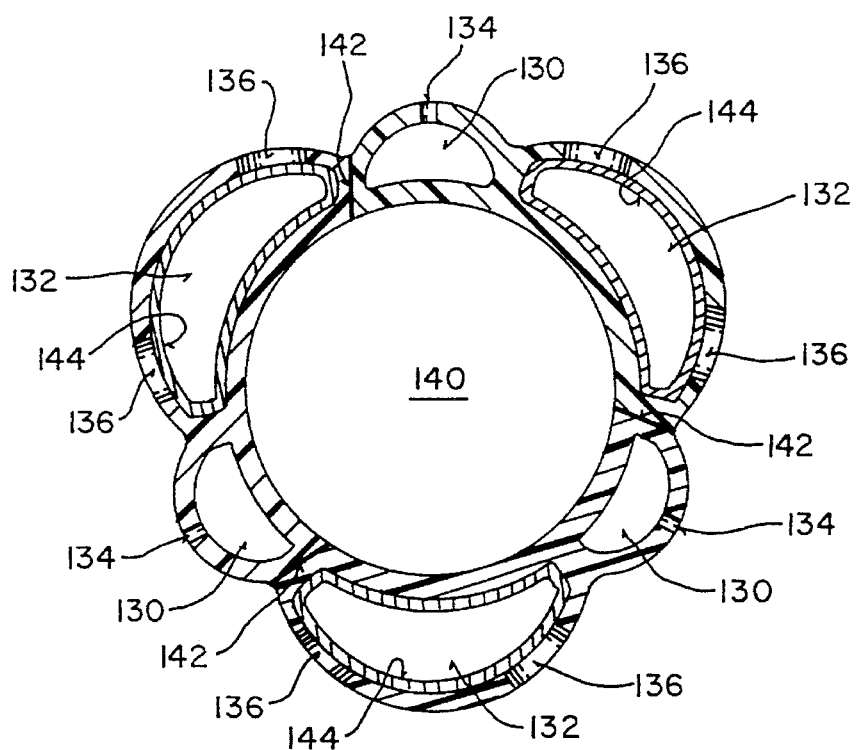
FIG. 8 is a cross-sectional view of the catheter sleeve of FIG. 6, taken along line 8—8 of FIG. 6.

Referring now to FIGS. 6, 7, and 8, a preferred catheter sleeve 100 constructed in accordance with the principles of the present invention will be described. Catheter sleeve 100 includes both blood perfusion lumens and drug infusion lumens on a radially expansible portion thereof. In particular, catheter sleeve 100 includes a flexible tubular body 102 which extends from a proximal end 104 to a distal end 106 thereof. A soft, atraumatic tip 108 is provided at the distal end, and a proximal housing 110 is provided at the proximal end. Housing 110 includes a first access port 112 for introducing a conventional balloon angioplasty catheter therethrough and a second access port 114 for delivering a drug to be infused through the drug infusion lumens of the catheter sleeve.

The flexible catheter body 102 comprises a single extrusion having a central lumen 120 and three peripheral drug supply lumens 122. The drug supply lumens 122 are connected with the drug infusion port 114 in order to supply drugs to the distal end of the catheter sleeve 100.

A blood perfusion portion 126 of the catheter sleeve is provided at the distal end of the flexible tube body 102. The blood perfusion portion 126 will be formed as a separate extrusion and will be attached to the distal end of the proximal portion of the body, typically by thermal fusion, adhesives, ultrasonic welding, or the like. The blood perfusion portion 126 includes both drug infusion lumens 130 (FIG. 8) and blood perfusion lumens 132. The drug infusion lumens 130 include a plurality of infusion ports 134, and the blood perfusion lumens 132 include a plurality of proximal inlet ports 136 (FIG. 6) and intermediate and distal outlet ports 138. A radially expansible region within the blood perfusion portion 126 further includes a central lumen 140 which receives the balloon of a balloon dilatation catheter, as described in more detail hereinafter. The radially expansible region is slit along lines 142 to permit radial expansion, as best observed in FIG. 8. The slits 142 may extend along the entire length of the blood perfusion portion 126, but more typically will be disposed only in the distal 1.5 cm to 5.0 cm, usually 2.0 cm to 3.0 cm, where the balloon will be disposed. Conveniently, radiopaque markers 127 may be provided in the catheter body to delineate the radially expansible region and facilitate placement of the sleeve over a dilatation balloon catheter.

The blood perfusion portion 126 will have a length in the range from about 5 cm to 25 cm, preferably being from about 7.5 cm to 15 cm, with the expansible portion being selected to be compatible with conventional balloon angioplasty catheters, e.g. less than 5 cm, usually in the range from 2 to 3 cm. Conventional dilatation balloons are available commercially from vendors such as Advanced Cardiovascular Systems, Inc., Temecula, Calif. By providing three drug infusion lumens 130 and three perfusion lumens 132, and splitting the radially expansible portion between adjacent drug/perfusion lumen pairs, as illustrated in FIG. 8, each drug infusion/blood perfusion lumen pair will have a common wall therebetween. Reliance on a common wall increases the cross-sectional area available for infusion/perfusion lumens in that region. FIG. 8 also discloses reinforcement members 144 disposed with each of the blood perfusion lumens 132. Conveniently, the reinforcement member will be in the form of a flat metal helix which extends the entire length of the lumen 132, where perfusion ports 136 are aligned with spaces between adjacent turns of the helix.

In the preferred embodiment of FIG. 6, blood perfusion lumens 132 are sealed at each end. At the proximal end, the blood perfusion lumens 132 are sealed by pinching off an otherwise open end of the lumen. The lumens are sealed at the distal end by the flexible tip 108. The drug infusion lumens 130 are aligned coaxially with and adjoined to the lumens 122 on the proximal portion of the flexible catheter body 102 Additionally, the blood perfusion lumens 132 are shown to have a greater area than the infusion lumens 130 Typically, the combined areas of the three perfusion lumens 132 will be at least 0.5 mm$^2$ preferably being from 10 mm$^2$ to 1.3 mm$^2$, or greater, in order to provide a sufficient perfusion flow rate The combined area of the drug infusion lumens is less critical, typically being from 0.05 mm$^2$ to 0.2 mm$^2$.

Figure 9A:
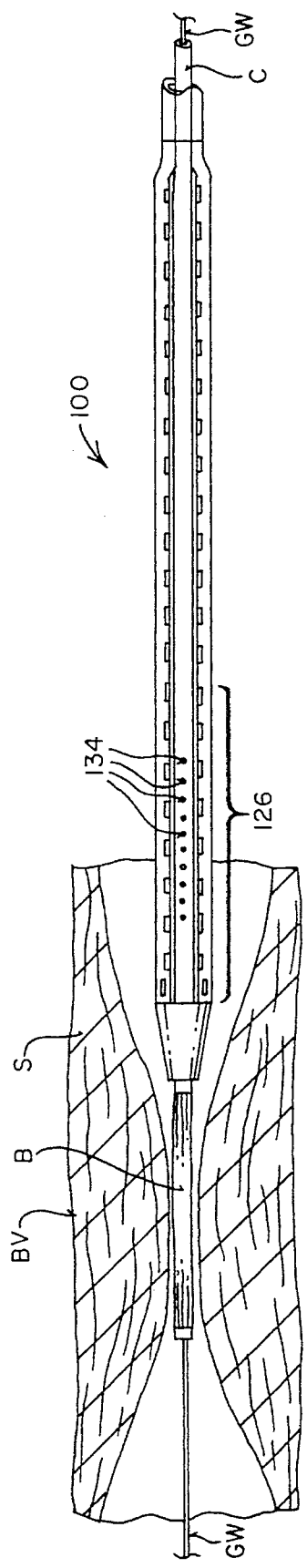

Referring now to FIGS. 9A–9D, use of the catheter sleeve 100 for delivering drugs after a conventional angioplasty procedure will be described An angioplasty catheter C is introduced so that a balloon B lies within a region of stenosis S in a blood vessel BV. The catheter sleeve 100 may be introduced simultaneously with the balloon catheter C, typically being disposed over a proximal portion of the catheter as illustrated in FIG. 9A. In either case, the catheter C or the catheter/catheter sleeve combination, will be introduced over a guidewire under fluoroscopic observation using conventional techniques.

Figure 9B:
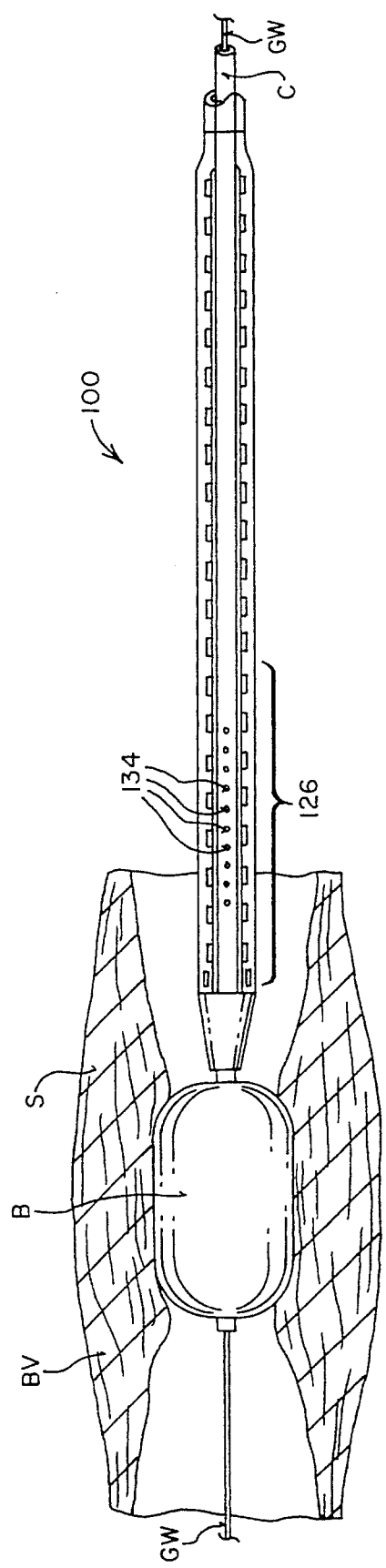

Once in place, the balloon B may be inflated to distend the vessel in the region of stenosis S, as illustrated in FIG. 9B. The catheter sleeve 100 will usually be disposed proximal to the balloon in order to be ready for use after the initial angioplasty procedure is completed.

Figure 10:
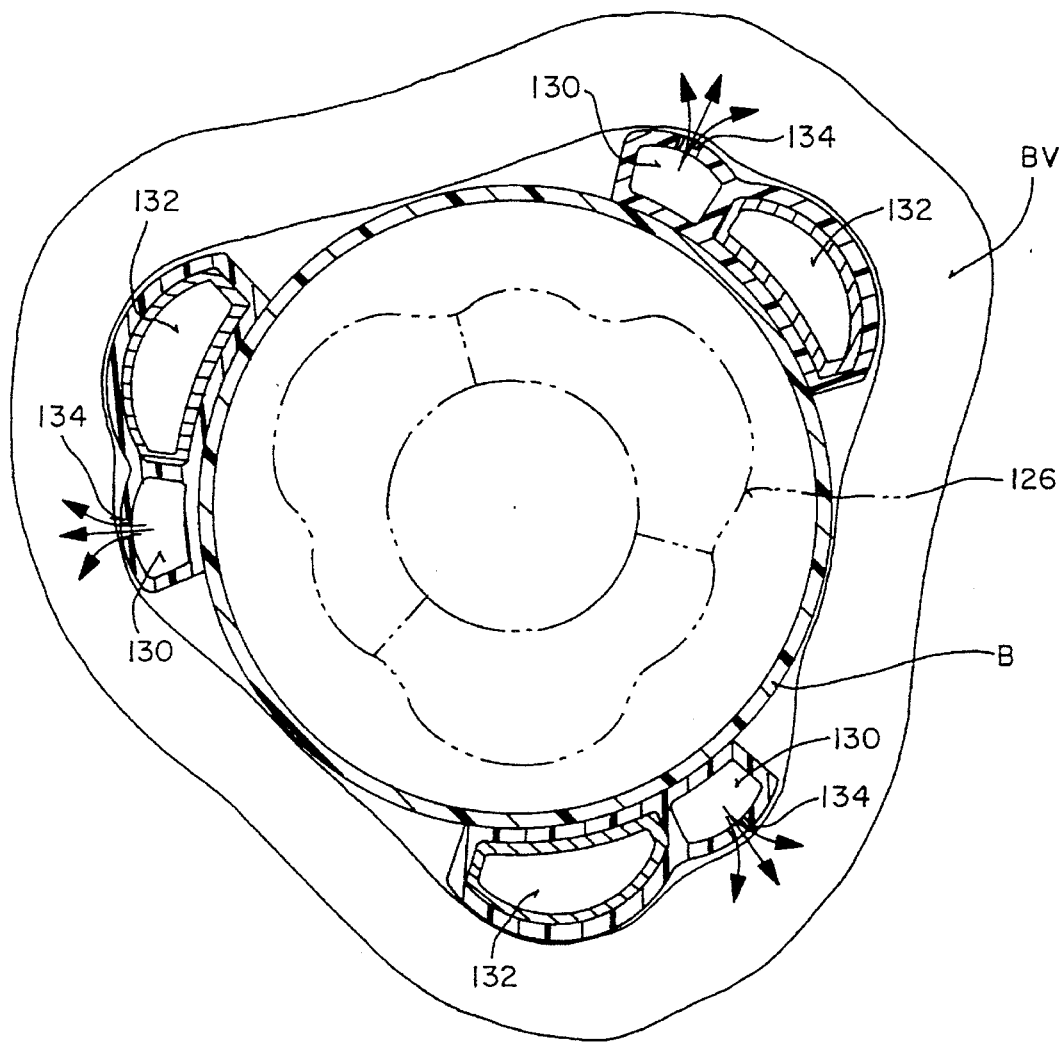
FIG. 10 is a cross-sectional view taken along line 10—10 of FIG. 9D.

After completing the angioplasty procedure, the balloon B is deflated, and the catheter sleeve 100 advanced distally or the balloon B is drawn proximally so that the radially expansible portion 126 lies over the angioplasty balloon. After properly positioning the balloon B and the catheter sleeve 100, as illustrated in FIG. 9C, the balloon B is inflated within the radially expansible portion 126 of the sleeve so that the drug infusion lumens 130 and blood flow perfusion lumens 132 are brought into contact with the inner wall of the blood vessel, as illustrated in FIG. 9D. Once in the radially expanded state, the blood flow perfusion lumens 132 provide a perfusion flow path, with blood entering through ports 136 and leaving through ports 138, as indicated by the arrows in FIG. 9D. At the same time, the drug infusion lumens 130 permit drug delivery through the infusion ports 134, as best illustrated in FIG. 10, which is a cross-sectional view taken along line 10—10 of FIG. 9D. FIG. 10 also illustrates (in broken line) the outline of the radially expansible region 126 of catheter sleeve 100, in the non-expanded configuration.

The catheter sleeve 100 may be further modified to provide additional capabilities and advantages, as will now be described. For example, the proximal region (shaft) of the catheter body may include a plurality of apertures 150 along its entire length (FIG. 6) in order to enhance the flow of a fluid, such as contrast media, through a guiding catheter when the catheter sleeve is present in a guiding catheter. The catheter sleeve of the present invention will necessarily have a larger diameter or "profile" than the balloon angioplasty catheter over which it is introduced. Thus, a greater portion of the cross-sectional area of the internal lumen of a guiding catheter will be occupied when the catheter sleeve is in use. While this results in a loss of luminal area for delivering contrast media and the like through the guiding catheter, such loss of area can be ameliorated by providing the ports 150 in the catheter body 102. Ports 150 allow fluid access to the annular space between the angioplasty balloon catheter and the inner luminal wall of the catheter sleeve, thus providing up to 15% or more cross-sectional area for the delivery of fluids therethrough.

Figure 11:
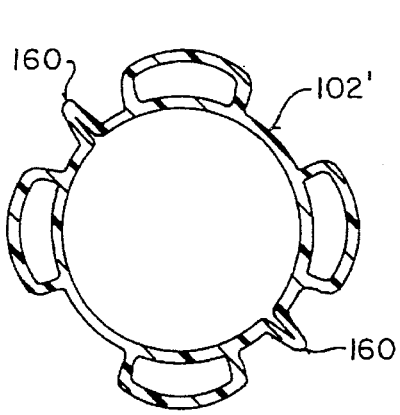
FIGS. 11–15 illustrate optional modifications of the catheter of FIGS. 1 and 6, where the shaft of the catheter has a reduced diameter.
Figure 12:
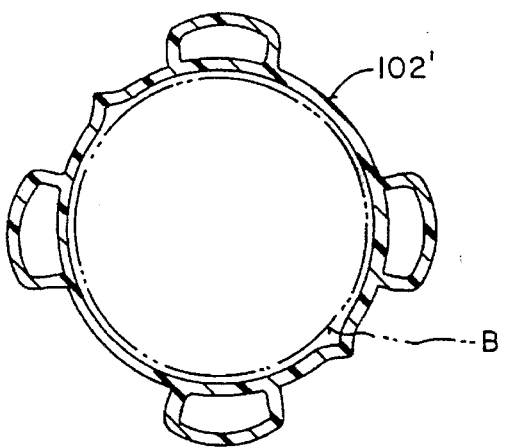

Further modifications of the proximal region of the flexible catheter body 102 are illustrated in FIGS. 11–14. The catheter body 102 needs to be sufficiently large in order to accommodate the dilatation balloon and other protuberances on the balloon angioplasty catheter which is to be introduced therethrough. By providing a catheter tube body 102' which is resiliently expansible, the outer profile of the catheter within the guiding catheter may be kept small while still permitting entry of the dilatation catheter. For example, as illustrated in FIGS. 11 and 12, the catheter tube body 102' may include one or more axial pleats 160 along its length so that the effective diameter can increase as a larger device (or portion of a device), such as folded balloon B shown in broken line in FIG. 12, is introduced therethrough. After the larger device or device portion has passed, the catheter body 102' will return to its reduced diameter, as illustrated in FIG. 11, thus leaving a larger area in the guiding catheter which is available for the passage of contrast media.

Figure 13:
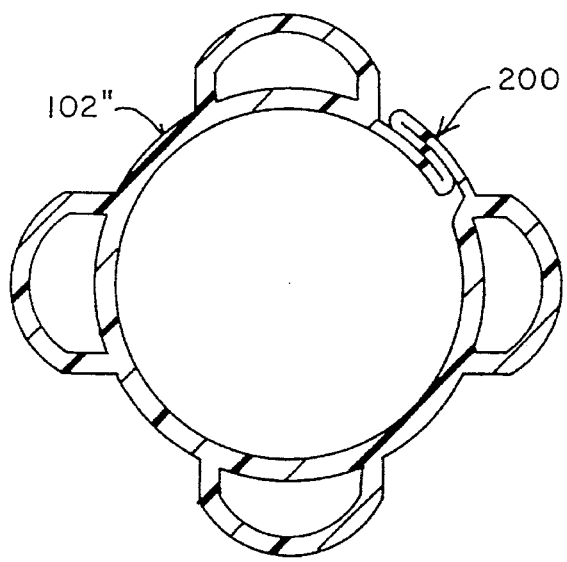
Figure 14:
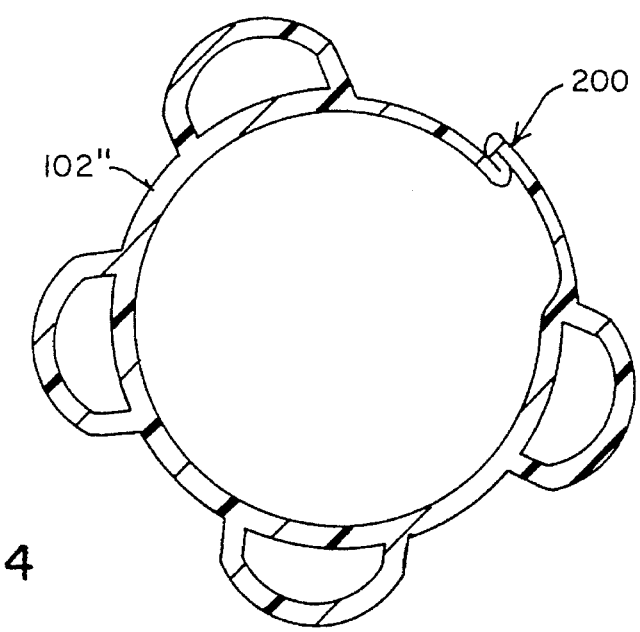

Such expansibility on the proximal portion of the catheter shaft may also be provided by including an involuted fold 200 in catheter body 102" as illustrated in FIGS. 13 and 14. The web between adjacent perfusion lumens may be thinned in the region where the fold is to be provided, typically being half as thick as the web in the other regions of the catheter body 102', and the web may be folded over as illustrated in FIG. 13. As a balloon angioplasty catheter or other device is passed through the lumen of the catheter body 102", the fold 200 will unfurl to allow passage for example of an enlarged distal end of the catheter, as illustrated in FIG. 14. After the enlarged portion has passed, the catheter body 102" will return to its original folded configuration, as illustrated in FIG. 13.

Figure 15:
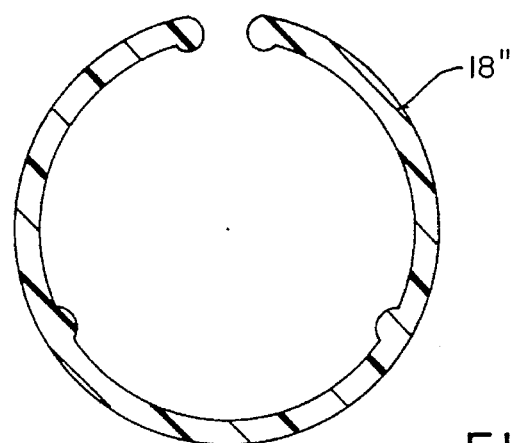

An alternative reduced-diameter configuration of the catheter body of FIG. 1 is illustrated in FIG. 15. A modified proximal portion 18" of the catheter body is axially split along its length in order to allow passage of an enlarged distal portion of a catheter to pass through its lumen. Optionally, the catheter body may be reinforced with wire or other resilient elements to maintain the profile as illustrated in FIG. 15.

The ability to introduce an angioplasty catheter into a catheter sleeve having a relatively small clearance between its inner luminal wall and the outer surface of the folded balloon or other protuberances on the angioplasty catheter shaft, is influenced by the closeness of the fit, friction between the contacting materials, the presence of fluid between the catheter and the catheter sleeve, and the length of engagement between the catheter and the catheter sleeve.

The catheter sleeve 100 may be further modified to provide a larger clearance for the angioplasty balloon catheter over the proximal-most approximately three-quarters of the catheter sleeve, thus reducing the length of engagement over the tightest one-quarter of the catheter sleeve length and enhancing the ability to introduce an angioplasty catheter therethrough. The incremental loss in luminal area between the inner luminal wall of the guiding catheter and the out surface of the catheter sleeve can then be compensated for by addition of ports 150, as described earlier.

Figure 17:
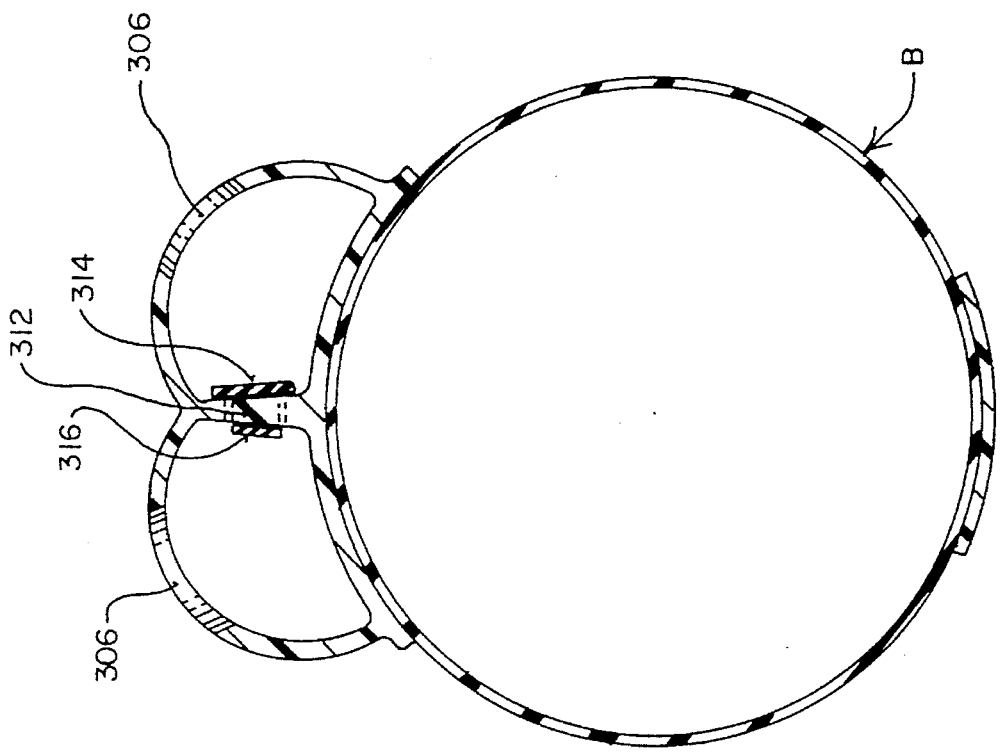
FIG. 17 is a cross-sectional view of the catheter sleeve of FIG. 16 shown on an inflated balloon in its expanded configuration.
Figure 16:
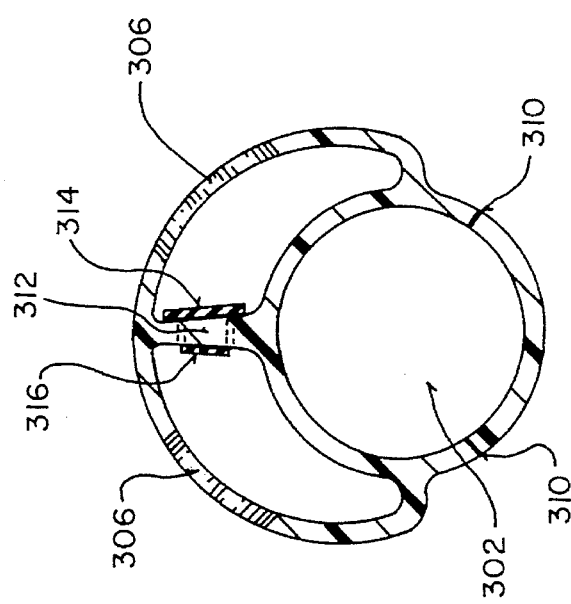
FIG. 16 is a cross-sectional view of a blood perfusion catheter sleeve similar to FIG. 1, having a single pair of adjacent perfusion lumens on one side of its distal end.
Figure 18:
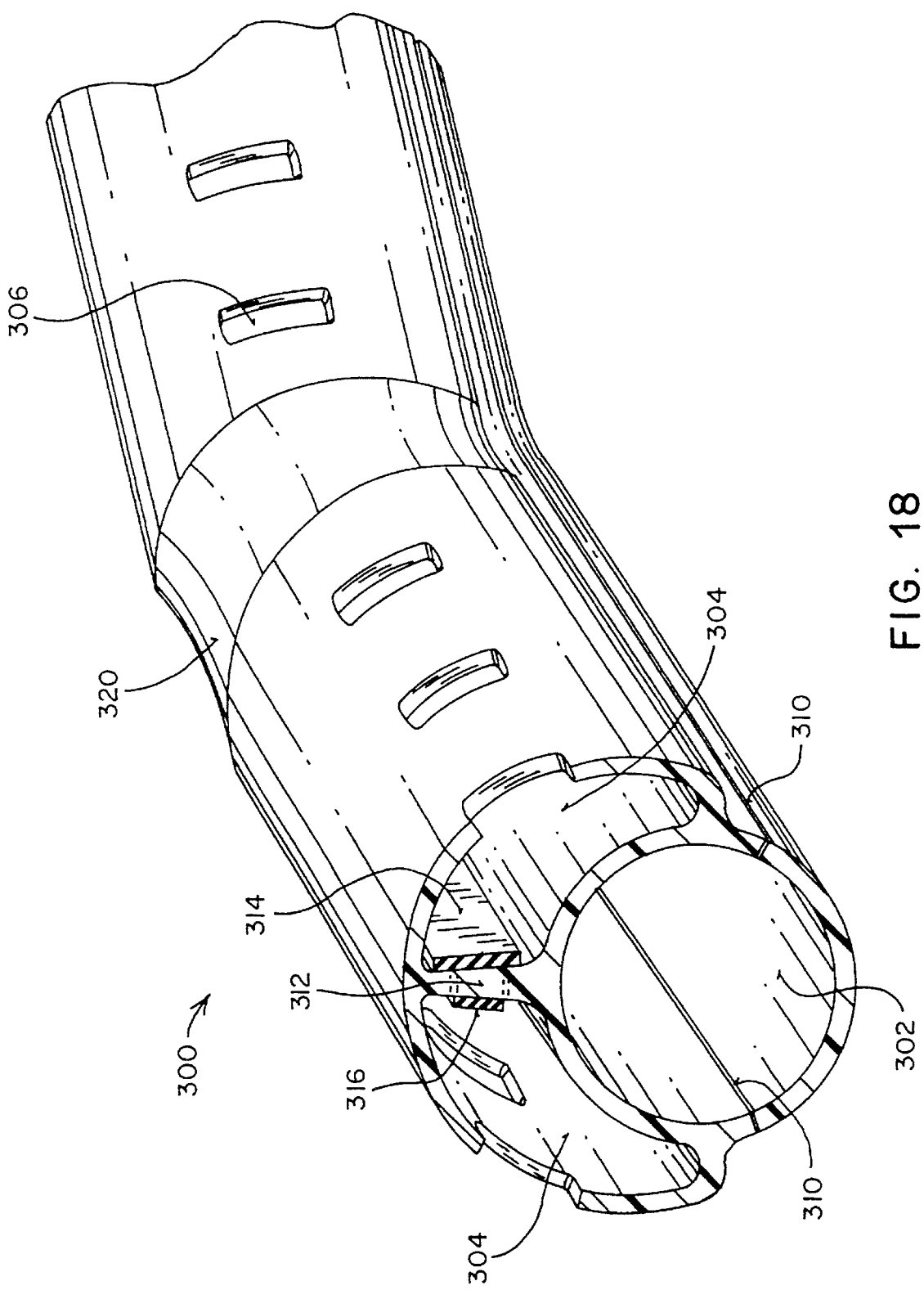
FIG. 18 is a partial, perspective view of the catheter of FIG. 16, showing an optional hinge structure.

A distal portion of a perfusion catheter sleeve 300 is illustrated in FIGS. 16–18. The catheter sleeve 300 includes a primary lumen 302 and a pair of adjacent perfusion lumens 304 having a plurality of perfusion ports 306 spaced-apart thereon. The web of the catheter body will be split along lines 310 to permit radially expansion by internal inflation of an angioplasty balloon B, as illustrated in FIG. 17. A septum 312 separates the perfusion lumens 304 and acts to reinforce the perfusion lumens to inhibit compression and collapse of the lumens during use. A radiopaque marker 314 is attached to the septum 312, typically by stapling to the septum or by folding one or more tabs 316 through a slot and over on the opposed face of the septum.

The catheter sleeve 300 has particular advantages. First, it can accommodate a wide range of artery sizes, typically, from 2 mm to 4 mm and larger. Second, the profile of adjacent lumens 304 is such that their available crosssectional areas increase as the sleeve is radially expanded. By comparing FIGS. 16 and 17, it can be seen that the portion of the catheter body web underlying the perfusion lumens flattens as the underlying balloon B is expanded. This results in the lumens opening up to provide an increased area for blood perfusion flow.

The catheter sleeve 300 may be modified to enhance flexibility by providing thinned hinge regions or joints 320, as illustrated in FIG. 18. Such articulations allow the catheter body to bend and flex more readily while maintaining the stiffness of the luminal segments and without reducing the available luminal cross-sectional area.

A further modification of the design of the catheter 300 is illustrated in FIGS. 18A–18C. A modified catheter 400 includes a primary lumen 402 and a pair of adjacent perfusion lumens 404 having a plurality of perfusion ports 406 spaced-apart thereon. A septum 412 separates the perfusion lumens 404 and acts to reinforce the perfusion lumens to inhibit compression and collapse during use. A radiopaque marker 414 and an attachment plate 416 are attached to the septum 312 using staples, rivets, or equivalent fasteners. As described thus far, the construction of catheter 400 is similar to that of catheter 300.

Catheter 400 further includes a plurality of spacer bars 420 formed axially over the expansible region of the catheter and separated by splits 422 formed in the web of the catheter. Thus, when the catheter 400 is expanded over an angioplasty balloon B (FIG. 18C), each of the spacer bars 420 will separate from the others and from the perfusion channels 404. The spacer bars 420 will form axial perfusion gaps 430 between the exterior surface of balloon B and interior wall of the artery A.

As illustrated in FIGS. 18A and 18C, the spacer bars have solid cross-sections which can readily be formed in the extrusion of the catheter body. It would also be possible to form miniature balloon spacers 440, as illustrated in FIG. 18B. The spacers 440 would each have a lumen 442 which would be connectable to a pressurized inflation source. The spacers 440 could thus be deployed and stiffened by internal pressurization, as shown in broken line in FIG. 18B. Use of balloon spacers can be advantageous since the profile of the catheter will be reduced during introduction and withdrawal when the balloons need not be inflated.

Figure 18D:
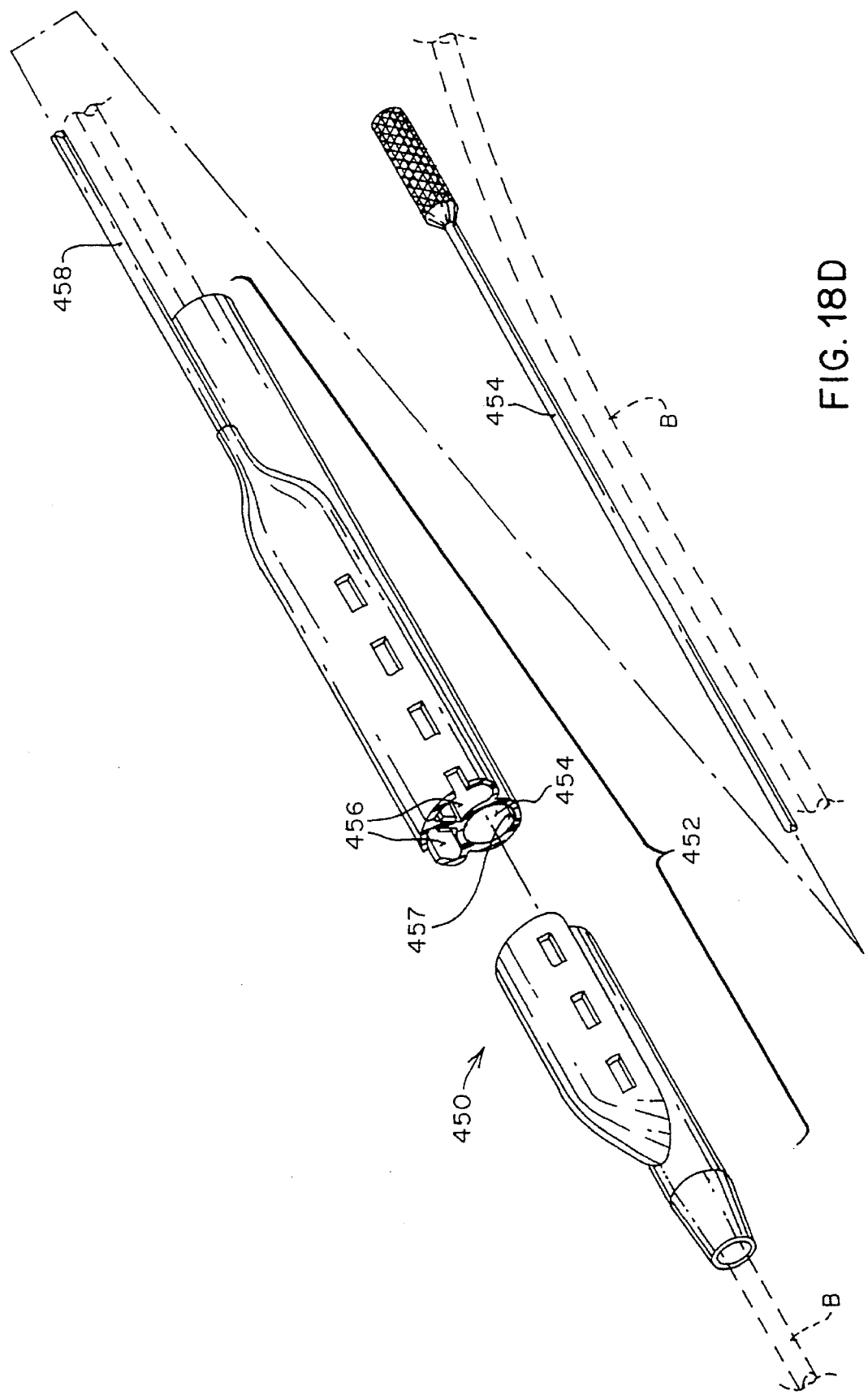
FIG. 18D illustrates a blood perfusion catheter sleeve similar to that illustrated in FIGS. 16–18, where the proximal portion of the sleeve is replaced with a connecting rod or tube.

Still a further modification of the design of the catheter 300 is illustrated in FIG. 18D. Catheter 450 includes a distal sleeve portion 452 having a cross-section identical to that of catheter 300. A primary lumen 454 and a pair of adjacent perfusion lumens 456 extend over the distal sleeve portion 452 which has a length in the range from 5 cm to 50 cm, usually from 5 cm to 25 cm. A single slit 457 in the primary lumen 454 allows for expansion of the distal sleeve in the region of the dilatation balloon. A connecting rod 458 is attached to the proximal end of the sleeve portion 452 and permits axial reciprocation of the sleeve relative to the balloon dilatation catheter B over which it has been introduced. The balloon dilatation catheter B is received within the primary lumen 454, as described with the previous embodiments, but the connecting rod 458 extends proximally from the sleeve portion 452 in parallel with the proximal shaft of the balloon dilatation catheter. It will be appreciated that substitution of such a connecting rod may be used in any of the preceding embodiments which do not provide for drug infusion. For embodiments that provide for drug infusion, it will be possible to substitute a narrow diameter tube (e.g. hypotube) of comparable diameter which can provide a drug supply lumen. The connecting rod 458 will usually be a flexible metal rod, typically stainless steel, having a diameter in the range from 0.3 mm to 0.8 mm.

The use of a small diameter connecting rod 458, or equivalent hypotube structure, is advantageous in that available lumen area within the guiding catheter for introduction of contrast media and other purposes is increased. Thus, the embodiment of FIG. 18D can be viewed as an alternative to the embodiments of FIGS. 11–15.

A distal portion of a catheter sleeve 500 having a hydraulically stiffened perfusion lumen structure 502 is illustrated in FIGS. 19–22. The catheter sleeve 500 can also include one or more drug infusion tubes 504 over its exterior surface (with one being illustrated in FIG. 19), although the drug infusion tube(s) would not be necessary in a catheter sleeve intended for perfusion only. The distal portion of the catheter sleeve 500 will be helically split along line 506 in order to allow radial expansion with an internal balloon catheter, as generally described for previous embodiments.

The first unique feature of the catheter sleeve 500 is the triple-lumen structure 502, illustrated in FIGS. 19–22. The perfusion lumen structure 502 includes a primary perfusion lumen 510 flanked by a pair of adjacent distally closed lumens 512 which may be inflated and stiffened with an incompressible fluid, e.g. contrast media or saline, in order to support the primary lumen 510. An expansible distal portion of the primary lumen 510 includes perfusion ports 514 in order to provide blood perfusion, as generally described with the prior embodiments.

Figure 19:
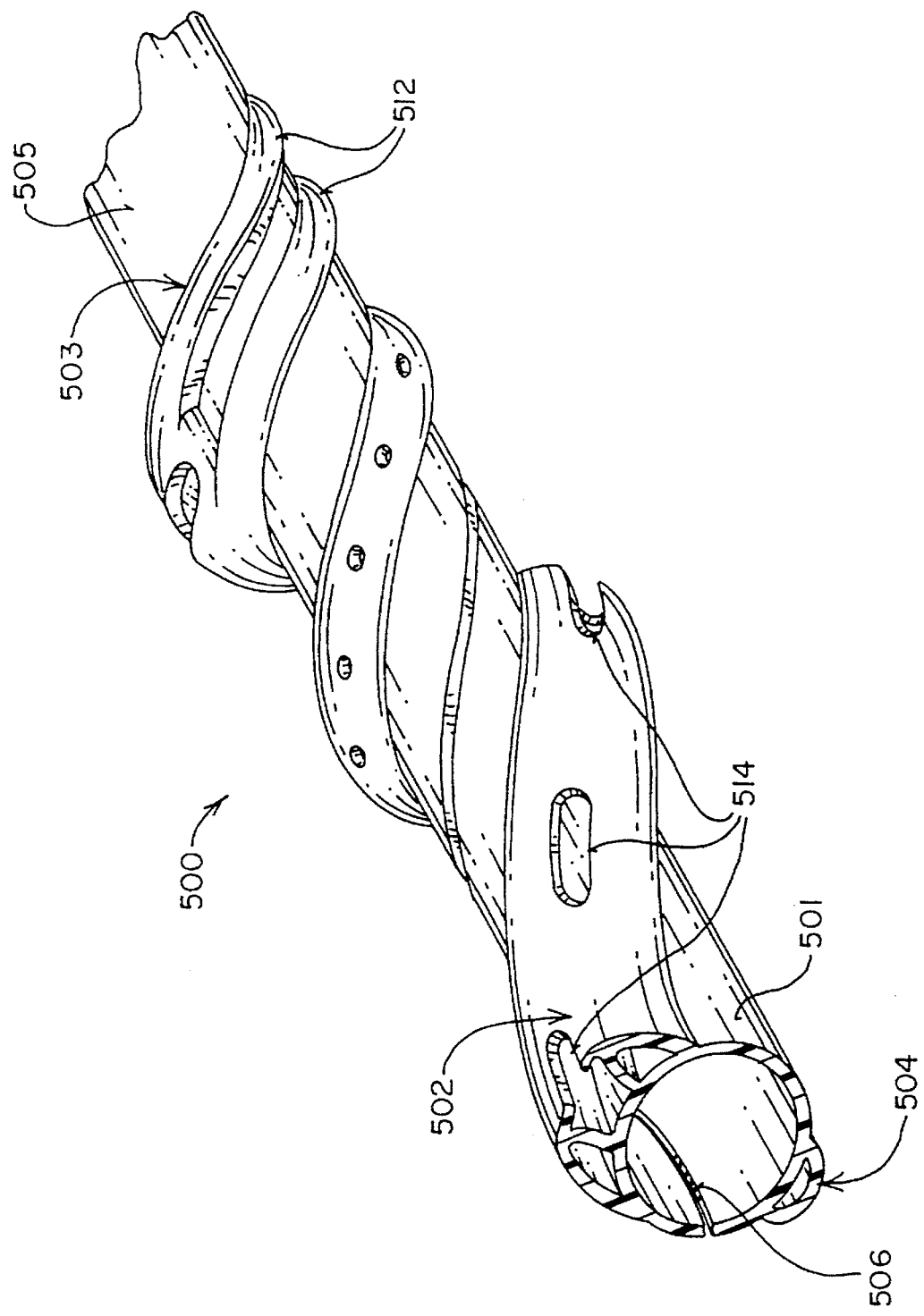
FIG. 19 is a perspective view with portions broken away of the distal end of a blood perfusion catheter having helical perfusion and drug infusion lumens, where the perfusion lumens may be hydraulically stiffened.
Figure 20:
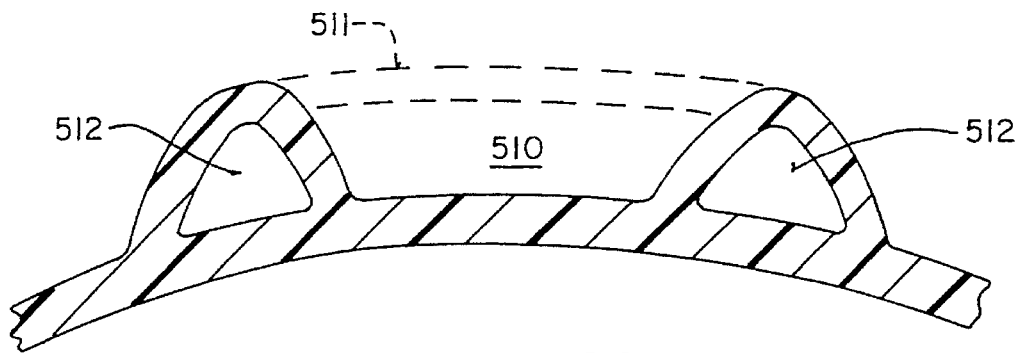
FIGS. 20–22 are cross-sectional views of the perfusion lumen of the catheter of FIG. 19.
Figure 21:
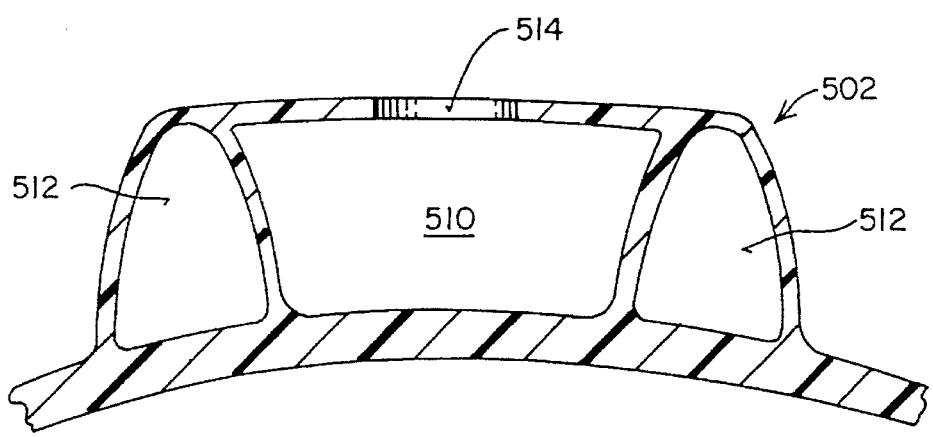
Figure 22:
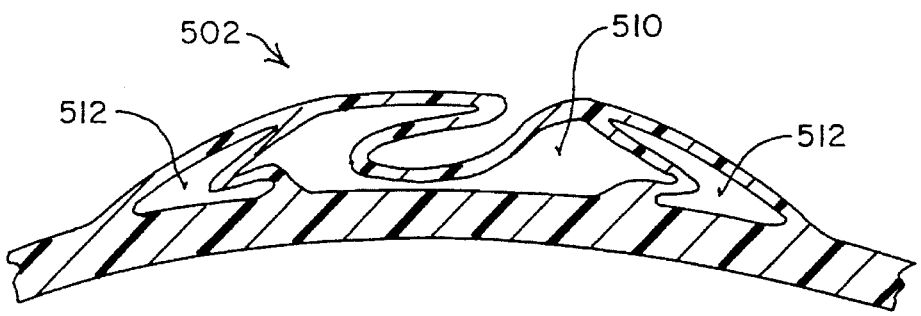

The expansible distal portion 501 and a transitional region 503 to the non-expansible proximal portion 505 of the catheter sleeve 500 are illustrated in FIG. 19. It will be appreciated that the primary lumen 510 need not be provided on the proximal portion of the catheter sleeve 500. It will, however, be necessary to provide extensions of the inflatable lumens 512. Conveniently, the inflation lumens 512 may be formed on the proximal portions of the catheter 500 as illustrated in FIGS. 19 and 20. An extrusion with a wall thickness of 0.08 to 0.2 mm is initially formed including all three lumens 510 and 512 of the triple-lumen structure 502. The top 511 of the primary lumen 510 (shown in broken line in FIG. 20) can then be removed, leaving a two-lumen structure. As part of the manufacturing process the distal portion of the triple-lumen 502 structure can then be expanded by internal pressurization under heat to form the enlarged structure of FIG. 21. Such heat expansion techniques are well known in the field of catheter construction, e.g. in the fabrication of non-compliant dilatation balloons. The distal ends of the inflation lumens 512 can then be sealed. Perfusion ports 514 may then be formed in the primary perfusion lumen 510. The resulting triple-lumen structure 502 will thus have a very thin and flexible wall with a thickness from 0.025 mm to 0.04 mm when not inflated. Advantageously, the thin-walled structure will be collapsible so that the triple-lumen structure can be folded as illustrated in FIG. 22. When inflated with a suitable pressure, typically from 1 atm to 10 atm, the perfusion lumen structure 502 will unfurl to provide an expanded blood perfusion path.

The use of a helical perfusion lumen structure 502 and a helical drug infusion tube 504 is advantageous since they facilitate aligning perfusion holes with side branches in the arterial vasculature and distributing drugs more evenly around an arterial lumen. The catheters of the present invention will usually be non-reinforced, making it difficult to rotate their distal ends by turning the proximal end. Thus, for catheter sleeves having axially aligned perfusion tube structures, such as illustrated in FIG. 1, it may sometimes be difficult to rotate the distal end of the catheter in order to perfuse a particular arterial side branch. By providing helical perfusion tubes having a fairly tight helical pitch, it will be appreciated that perfusion ports 514 may be provided in substantially all radial directions. Thus, by axially translating the catheter sleeve 500 within an artery, it will usually be possible to locate at least one perfusion port 514 which is properly radially aligned with a given arterial side branch.

Figure 23:
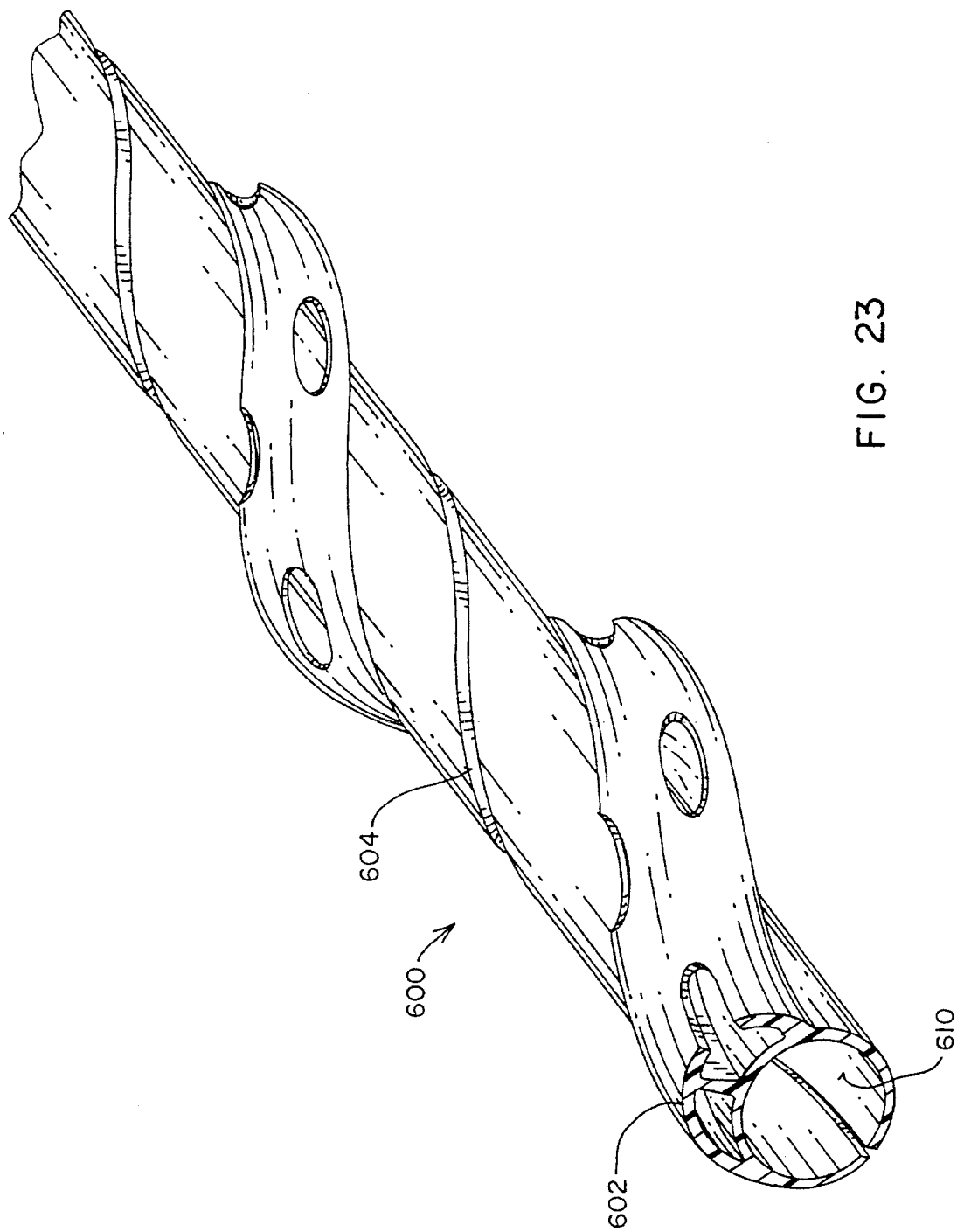
FIG. 23 illustrates an additional embodiment of a blood perfusion catheter sleeve according to the present invention having a pair of helically arranged perfusion lumens and a helical expansion slot.

An additional embodiment of the distal end of a catheter sleeve 600 is illustrated in FIG. 23. The catheter sleeve 600 includes a single helical pair of perfusion tubes 602 and a slot 604. Such a helical structure has generally the same advantages as described above in connection with catheter sleeve 500. The slot 604 will typically have a width in the range from about 0.1 mm to 0.5 mm, and will provide a high degree of flexibility and expansibility in the distal region of the catheter sleeve 600. The central lumen 610 of the catheter sleeve 600 may extend the entire length of the catheter sleeve, or the catheter sleeve may be attached to a connecting rod similar to rod 454 illustrated in FIG. 18D. The use of helical perfusion tubes (and optionally drug infusion tubes) is particularly preferred with embodiments employing connecting rods since the rotational alignment of the distal ends of such structures is very difficult.

The catheter sleeves of the present invention are suitable for delivery of a variety of therapeutic agents including pharmaceuticals, proteins, peptides, nucleotides, carbohydrates, polysaccharides, mucopolysaccharides, simple sugars, glycosaminoglycans, steroids, and the like. The drugs will be liquid soluble or dispersable in a suitable liquid carrier in order to be delivered through the drug infusion lumens of the catheter sleeve. The drugs may be present in a variety of formulations, including dissolved or dispersed, as just described, or present in a variety of carriers, such as microcarriers, liposomes, and the like. The catheter sleeves of the present invention may also be suitable for delivering other biological substances, such as genetic material and suitable vectors to effect genetic transformation. The catheter sleeves will preferably be used for delivering drugs having direct benefit to the cardiovascular system, including antithrombotics, antiplatelets, antimetabolics, growth factor inhibitors, anticoagulants, antimitotics, antibiotics, and the like.

Although the foregoing invention has been described in some detail by way of illustration and example, for purposes of clarity of understanding, it will be obvious that certain changes and modifications may be practiced within the scope of the appended claims.

What is claimed is:

1. A catheter sleeve comprising:
    a flexible tubular body having a proximal end, a distal end, and a central lumen therethrough, wherein at least a portion of the tubular body is radially expansible as a result of a radial expansion force applied in the central lumen within said portion; and
    at least one perfusion lumen disposed over said radially expansible portion of the tubular body, wherein said lumen has a plurality of axially spaced-apart ports distributed substantially uniformly over its length which permit blood flow through the lumen.

2. A catheter sleeve comprising:
    a flexible tubular body having a proximal end, a distal end, and a central lumen therethrough, wherein at least a portion of the tubular body is radially expansible as a result of a radial expansion force applied in the central lumen within said portion; and
    one or more channels disposed over said radially expansible portion of the tubular body, wherein the channels define flow paths between the tubular body and a surrounding blood vessel wall.

3. A catheter sleeve as in claim 1 or 2, wherein the tubular body is radially expansible over a length in the range from about 1.5 cm to 5 cm near the distal end.

4. A catheter sleeve as in claim 3, wherein the tubular body has a diameter which is radially expansible to a diameter of 5 mm.

5. A catheter sleeve as in claim 1, further comprising structure in at least one of the lumens to reinforce said lumen to prevent compression or collapse of the lumen.

6. A catheter sleeve as in claim 3, wherein the reinforcing structure comprises a helical wire supporting the interior of the lumen.

7. A catheter sleeve as in claim 1, further comprising additional lumens having means for infusing therapeutic agents therethrough.

8. A catheter sleeve as in claim 7, wherein the lumens having therapeutic agent infusing means are paired with lumens having perfusion flow means with a common wall therebetween, wherein the tubular body is slit between adjacent pairs.

9. A catheter sleeve as in claim 8, wherein the tubular body is slit between adjacent lumen pairs along a length in the range from 1.5 cm to 5 cm near the distal end.

10. A catheter sleeve as in claim 1, including at least two perfusin lumens wherein the tubular body is slit between the lumens to enhance radial expansibility.

11. A catheter sleeve as in claim 1, wherein substantially the entire length of the tubular body is radially expansible.

12. A catheter sleeve as in claim 8 wherein a proximal portion of the catheter body is pleated, rolled, or slit to facilitate passage of a large diameter portion of a balloon catheter through the central lumen.

13. A catheter sleeve as in claim 1, wherein a proximal portion of the flexible tubular body has side ports to enhance the flow of perfusion liquid through a guiding catheter when the catheter sleeve is in place therein.

14. A catheter sleeve as in claim 1, wherein the perfusion-flow-establishing means comprise helically arranged flow paths.

15. A catheter sleeve as in claim 14, further comprising at least one helical drug infusion tube formed over the radially expansible portion of the tubular body.

16. A catheter sleeve as in claim 14, wherein the tubular body is helically split between said flow paths.

17. A catheter sleeve as in claim 1, wherein the perfusion-flow-establishing means comprises a pair of adjacent lumens formed on one side of the tubular body, wherein the lumens are separated by a common septum and are split from the remainder of the tubular body to permit radial expansion.

18. A catheter sleeve as in claim 17, further comprising a radiopaque marker attached to the septum.

19. A catheter sleeve as in claim 18, wherein the radiopaque marker comprises a pair of plates secured to each other on opposite sides of the septum.

20. A catheter sleeve as in claim 17, further comprising a plurality of axial spacers on a side of the tubular body opposite to the pair of adjacent lumens.

21. A catheter sleeve as in claim 20, wherein the spacers have solid cross-section.

22. A catheter sleeve as in claim 20, wherein the spacers are inflatable.

23. A catheter sleeve as in claim 1, further comprising a rod having a diameter less than that of the tubular body attached to a proximal end of the tubular body.

24. A catheter sleeve as in claim 17, wherein axially spaced-apart hinges are formed in the tubular body along the adjacent pair of lumens to enhance flexibility.

25. A catheter sleeve as in claim 1, wherein the perfusion-flow-establishing means comprises a triple lumen blood perfusion tube formed over the tubular body, wherein a center lumen includes perfusion ports and the two flanking lumens are closed to permit inflation to selectively reinforce the center lumen.

26. A catheter sleeve as in claim 25, wherein the blood perfusion tube is arranged helically over the tubular body, further comprising a helical drug infusion tube disposed opposite to the blood perfusion tube over the tubular body, wherein the tubular body is split between the blood perfusion tube and the drug infusion tube to permit radial expansion.

27. A catheter sleeve as in claim 1, wherein the lumen has a plurality of axially spaced-apart ports which permit blood flow through the lumen.

28. A catheter sleeve as in claim 27, further comprising structure in at least one of the lumens to reinforce said lumen to prevent compression or collapse of the lumen.

29. A method for perfusing blood past a treatment site within a blood vessel, said method comprising:

positioning a sleeve having a central lumen at said treatment site, said sleeve defining at least one flow path thereover, wherein said flow path provides both axial flow and radially inward and outward flow over substantially its entire length; and applying a radial force within the central lumen to expand the sleeve within the treatment site while blood flows past the expanded sleeve through said at least one flow path and radially in and out of the flow path over substantially the entire expanded length of the sleeve.

30. A method as in claim 29, further comprising positioning a dilatation balloon catheter within a distal end of the sleeve and inflating said balloon to radially expand said sleeve.

31. A method as in claim 30, wherein the balloon is inflated to a pressure in the range from 0.5 atm to 16 atm.

32. A method as in claim 29, further comprising delivering a therapeutic agent to said treatment site through said sleeve while said sleeve is radially expanded.

33. A method as in claim 29, wherein the sleeve is positioned in the blood vessel so that blood flowing past the expanded sleeve enters a branch blood vessel.

34. A method as in claim 29, wherein the radially expanding step comprises inflating a balloon within the sleeve at low pressure for a prolonged period to preserve the initial inflation perimeter of the balloon.

35. A method for delivering a therapeutic agent to a treatment site on an interior wall of a blood vessel, said method comprising:

positioning a sleeve at said treatment site, said sleeve having a plurality of axial flow paths thereover;

radially expanding the sleeve to contact an exterior surface thereof against the interior wall of the blood vessel; and infusing the therapeutic agent through at least some of the flow paths to the blood vessel wall, wherein others of said flow paths establish blood perfusion past the radially expanded sleeve.

36. A method as in claim 35, further comprising positioning a balloon catheter within a distal end of the sleeve and inflating said balloon to radially expand said sleeve.

37. A method as in claim 36, wherein the balloon is inflated to a pressure in the range from 0.5 atm to 16 atm.

38. A method as in claim 35, wherein the sleeve is positioned at the treatment site after an angioplasty procedure has been performed at the same site.

39. An improved method for treating a target location within a blood vessel, said method being of the type wherein a balloon is expanded against an interior wall of the blood vessel, wherein the improvement comprises providing radially open perfusion flow paths over an outer surface of the balloon, whereby blood flow is established through said perfusion paths.

40. An improved method as in claim 39, further comprising providing drug infusion lumens disposed over an outside surface of the balloon and infusing a therapeutic agent therethrough to the target location.

41. An improved method as in claim 39, wherein the perfusion flow paths are provided by positioning a catheter sleeve over the balloon, wherein the catheter sleeve is radially expansible and includes said perfusion flow paths thereon.

42. An improved method as in claim 39, wherein the balloon is expanded by inflating to a pressure in the range from 0.5 atm to 16 atm.

43. A catheter sleeve comprising:

a flexible tubular body having a proximal end, a distal end, and a central lumen therethrough, wherein at least a portion of the tubular body is axially split to permit radial expansion as a result of a radial expansion force applied in the central lumen within said portion; and means over a radially expansible portion of the tubular body near the distal end for establishing blood perfusion flow.

44. A catheter sleeve as in claim 43, wherein the perfusion-flow-establishing means comprises at least one perfusion lumen disposed over said radially expansible portion of the tubular body, wherein said lumen has a plurality of axially spaced-apart ports which permit blood flow through the lumen.

45. A catheter sleeve as in claim 43, further comprising structure in at least one of the lumens to reinforce said lumen to prevent compression or collapse of the lumen.

46. A catheter sleeve as in claim 45, wherein reinforcing structure comprising a helical wire supporting interior of the lumen.

47. A catheter sleeve as in claim 44, including at least two prefusion lumens wherein the tubular body is slit between the lumens to enhance radial expansibility.

48. A catheter sleeve as in claim 43, wherein the perfusion-flow-establishing means comprises one or more channels disposed over said radially expansible portion of the tubular body, wherein the channels define flow paths between the tubular body and a surrounding blood vessel wall.

49. A catheter sleeve as in claim 43 or 48, wherein the tubular body is radially expansible over a length in the range from about 1.5 cm to 5 cm near the distal end.

50. A catheter sleeve as in claim 49, wherein the tubular body has a diameter which is radially expansible to a diameter of 5 mm.

51. A catheter sleeve as in claim 43, wherein a proximal portion of the flexible tubular body has side ports to enhance the flow of perfusion liquid through a guiding catheter when the catheter sleeve is in place therein.

52. A catheter sleeve as in claim 43, wherein the perfusion-flow-establishing means comprise helically arranged flow paths.

53. A catheter sleeve as in claim 52, further comprising at least one helical drug infusion tube formed over the radially expansible portion of the tubular body.

54. A catheter sleeve as in claim 52, wherein the tubular body is helically split between said flow paths.

55. A catheter sleeve as in claim 43, wherein the perfusion-flow-establishing means comprises a pair of adjacent lumens formed on one side of the tubular body, wherein the lumens are separated by a common septum and are split from the remainder of the tubular body to permit radial expansion.

56. A catheter sleeve as in claim 43, further comprising a rod having a diameter less than that of the tubular body attached to a proximal end of the tubular body.

57. A catheter sleeve as in claim 43, wherein the perfusion-flow-establishing means comprises a triple lumen blood perfusion tube formed over the tubular body, wherein a center lumen includes perfusion ports and the two flanking lumens are closed to permit inflation to selectively reinforce the center lumen.

58. A catheter sleeve as in claim 43, further comprising additional lumens having means for infusing therapeutic agents therethrough.

59. A catheter sleeve as in claim 58, wherein the lumens having therapeutic agent infusing means are paired with lumens having perfusion flow means with a common wall therebetween, wherein the tubular body is slit between adjacent pairs.

60. A catheter sleeve as in claim 59, wherein the tubular body is slit between adjacent lumen pairs along a length in the range from 1.5 cm to 5 cm near the distal end.

61. A method for perfusing blood past a treatment site within a blood vessel, said method comprising:

positioning a sleeve having a central lumen at said treatment site, said sleeve defining at least one flow path thereover and being axially split in the region of the flow path; and applying a radial force within the central lumen to expand the sleeve within the treatment site while blood flows past the expanded sleeve through said at least one flow path, wherein radial expansion causes circumferential separation of the axial split(s).

62. A method as in claim 61, further comprising positioning a dilatation balloon catheter within a distal end of the sleeve and inflating said balloon to radially expand said sleeve.

63. A method as in claim 61, wherein the balloon is inflated to a pressure in the range from 0.5 atm to 16 atm.

64. A method as in claim 61, further comprising delivering a therapeutic agent to said treatment site through said sleeve while said sleeve is radially expanded.

65. A method as in claim 61, wherein the sleeve is positioned in the blood vessel so that blood flowing past the expanded sleeve enters a branch blood vessel.

66. A method as in claim 61, wherein the radially expanding step comprises inflating a balloon within the sleeve at low pressure for a prolonged period to preserve the initial inflation perimeter of the balloon.

67. A catheter sleeve comprising:

a flexible tubular body having a proximal end, a distal end, and a central lumen therethrough, wherein at least a portion of the tubular body is radially expansible as a result of a radial expansion force applied in the central lumen within said portion; and at least one perfusion lumen integrally formed as a single extrusion as part of the tubular body near the distal end for establishing blood perfusion flow.

68. A catheter sleeve as in claim 67, wherein the tubular body is radially expansible over a length in the range from about 1.5 cm to 5 cm near the distal end.

69. A catheter sleeve as in claim 68, wherein the tubular body has a diameter which is radially expansible to a diameter of 5 mm.

70. A catheter sleeve as in claim 66, including at least two integrally formed perfusion lumens, wherein the tubular body is slit between the lumens to enhance radial expansibility.

71. A catheter sleeve as in claim 67, further comprising additional integrally formed lumens having means for infusing therapeutic agents therethrough.

72. A method for perfusing blood past a treatment site within a blood vessel, said method comprising:

positioning a sleeve having a central lumen at said treatment site, said sleeve including at least one perfusion lumen integrally formed as a single extrusion thereover; and applying a radial force within the central lumen to expand the sleeve within the treatment site while blood flows past the expanded sleeve through said at least one perfusion lumen.

73. A method as in claim 72, wherein the radially expanding step comprises inflating a balloon within the sleeve at low pressure for a prolonged period to preserve the initial inflation perimeter of the balloon.

74. A method as in claim 72, further comprising positioning a dilatation balloon catheter within a distal end of the sleeve and inflating said balloon to radially expand said sleeve.

75. A method as in claim 74, wherein the balloon is inflated to a pressure in the range from 0.5 atm to 16 atm.

76. A method as in claim 72, further comprising delivering a therapeutic agent to said treatment site through said sleeve while said sleeve is radially expanded.

77. A method as in claim 72, wherein the sleeve is positioned in the blood vessel so that blood flowing past the expanded sleeve enters a branch blood vessel.

78. A method for perfusing blood past a treatment site within a blood vessel, said method comprising:

inflating a balloon catheter to dilate a blood vessel treatment site to an initial inflation perimeter;

deflating the balloon;

positioning a sleeve having a central lumen over the deflated balloon at said treatment site, said sleeve defining at least one flow path thereover; and reinflating the balloon within the sleeve at low pressure in the range from 0.5 atm to 5 atm for a prolonged period to preserve the initial inflation perimeter of the balloon.

79. A catheter sleeve comprising:

a flexible tubular body having a proximal end, a distal end, and a central lumen therethrough, wherein at least a portion of the tubular body is radially expansible as a result of a radial expansion force applied in the central lumen within said portion;

means over a radially expansible portion of the tubular body near the distal end for establishing blood perfusion flow; and means over the radially expansible portion of the tubular body near the distal end for infusing therapeutic agents.

80. A catheter sleeve as in claim 79, wherein the perfusion-flow-establishing means comprises at least one lumen disposed over said radially expansible portion of the tubular body, wherein said lumen has a plurality of axially spaced-apart ports which permit blood flow through the lumen.

81. A catheter sleeve as in claim 80, wherein the tubular body is radially expansible over a length in the range from about 1.5 cm to 5 cm near the distal end.

82. A catheter sleeve as in claim 81, wherein the tubular body has a diameter which is radially expansible to a diameter of 5 mm.

83. A catheter sleeve as in claim 79, wherein the therapeutic agent infusing means comprises at least one infusion lumen having means for releasing the agent therethrough.

84. A catheter sleeve as in claim 83, wherein the lumens having therapeutic agent infusing means are paired with lumens having perfusion flow means with a common wall therebetween, wherein the tubular body is slit between adjacent pairs.

85. A catheter sleeve as in claim 84, wherein the tubular body is slit between adjacent lumen pairs along a length in the range from 1.5 cm to 5 cm near the distal end.

* * * * *